United States Patent [19]

Hoefelmayr et al.

[11] Patent Number: 5,094,112
[45] Date of Patent: Mar. 10, 1992

[54] PROCESS AND A DEVICE FOR CARRYING OUT MEASUREMENTS AT A FOAMING LIQUID

[75] Inventors: Tilman Hoefelmayr, Niederteufen; Dieter Schulz, Eching-Viecht, both of Fed. Rep. of Germany

[73] Assignee: Biomelktechnik Hoefelmayr & Co., Niederteufen, Switzerland

[21] Appl. No.: 727,659

[22] Filed: Jul. 9, 1991

Related U.S. Application Data

[62] Division of Ser. No. 268,025, Nov. 4, 1988, Pat. No. 5,035,139.

[30] Foreign Application Priority Data

Nov. 5, 1987 [DE] Fed. Rep. of Germany ....... 3737607

[51] Int. Cl.$^5$ ............................ G01F 11/28; A01J 7/00
[52] U.S. Cl. .................... 73/861.04; 73/223; 73/865; 119/14.17; 364/510
[58] Field of Search ...................... 73/861.04, 223, 865; 73/215; 119/14.15, 14.17; 364/510

[56] References Cited

U.S. PATENT DOCUMENTS

| | | | |
|---|---|---|---|
| 3,075,383 | 1/1963 | Favill et al. | 73/861.04 |
| 4,010,643 | 3/1977 | Dekan | 73/861.04 |
| 4,452,176 | 6/1984 | Hoefelmayr et al. | 119/14.17 |

Primary Examiner—Herbert Goldstein
Attorney, Agent, or Firm—Flynn, Thiel, Boutell & Tanis

[57] ABSTRACT

This specific density of the liquid/air mixture is measured at successive levels within the reception vessel for the liquid using a reference measurement ($I_o$) representing the specific density of the degasified liquid within a reference measuring path. The ratio of each obtained density value measurement and the reference value is calculated for each measuring level and multiplied with the specific density of the liquid to allow an accurate measurement of the overall liquid volume or flow-rate. Preferably the reception vessel (1) has a respective measuring electrode ($E_1..E_n$) at each measuring level with a common counter electrode ($E_o$) coupled to an oscillator (4) via a constant voltage circuit (5) and a coupling capacitor (6). Each measuring electrode ($E_1$-$E_n$) is coupled via a multiplexer (7) and an active rectifier (9) to an A/D converter (10) coupled to a microprocessor (11) controlling a read-out display (12).

52 Claims, 9 Drawing Sheets

PROCESS AND A DEVICE FOR CARRYING OUT MEASUREMENTS AT A FOAMING LIQUID

This is a division of Ser. No. 07/268 025, filed Nov. 4, 1988, now U.S. Pat. No. 5,035,139.

FIELD OF THE INVENTION

The invention relates to a process for carrying out measurements at foaming liquids in which a measuring value ($I_m$) depending on one parameter of the liquid is measured at the liquid contained in a vessel in each case at several different height levels. The invention relates also to a device for carrying out measurements at foaming liquids, in particular milk/air mixtures comprising a vessel and at least one measuring device with which a measuring value ($I_m$) depending on one parameter of the liquid contained in the vessel can be measured in each case at several different height levels of the vessel. The invention is in particular used in the measurement of the mass or the flow of foaming liquids and in particular of milk.

BACKGROUND OF THE INVENTION

When measuring milk quantities on the farm or in the dairy the mass of the milk is of interest. For this reason the weighing of the milk would be the right method for exactly determining the mass. However, an exact weighing of the milk is technically very difficult in the rough everday use in the stables on a farm, in particular, if only small, possibly mobile milk quantity measuring devices should to be used.

In such weighing devices the influences of force of the connected feed and discharge tubes, the kinetic energy of the obtained milk pulsating, vibrations due to careless handling, a non-horizontal measuring base, cleaning problems in internal measuring chambers with the necessary pressure compensation lines, etc. would entail considerable problems and also measuring errors. Therefore it is not astonishing that it was impossible for weighing milk quantity measuring systems to be successful in rural everyday practice outside of research institutes.

Practically all milk quantity measuring devices known at present attempt to ascertain the mass of the obtained milk by means of a volume measurement. Devices have become known which comprise for instance milk quantity measuring vessels firmly installed at the milking station or devices in which part of the milk flow is in each case put aside and measured. Socalled flow meters are also already known which work either intermittently batchwise or carry out a continuous quantity measurement.

An example of the first type of measurement is known from the DE-OS 30 05 489, in which the obtained milk is guided into a large storage vessel. A measuring probe is disposed in the storage vessel which comprises several measuring electrodes at the same height distance above each other which cooperate with a joint stationary counter-electrode. In this measuring process the property of the milk that is used is that it has a relatively great conductivity with respect to the insulator air to determine at different electrodes by means of the cyclic application of an electric field which electrode circuits are already closed due to the level of the milk. Thus each electrode circuits is interrogated regarding a yes/no decision in the sense that the electrode circuits located below the milk level give the information yes-closed, while the electrode circuits located above the milk level indicate the information no-not closed.

A process for the determination of the portions of three different fluids, namely water, crude oil and gas is known from the U.S. Pat. No. 3,530,711 in a completely different field, namely in the field of crude oil drillings. Electrodes being disposed in vertical staggered relationship with respect to each other are provided with a joint counter-electrode in a measuring pipe in which the sample taken can settle, whereby three separate layers and thus two boundary layers result due to the different density. The electrodes are cyclically interrogated with an a-c voltage and the capacity is measured in each case. Due to the different dielectric constants of water, crude oil and gas, the position of the respective boundary layers and thus the size of the respective volume can be determined at the boundary layers due to a jump in the size of the measured capacitance.

A process for the quantity determination of two galvanic liquids (liquids metals) stacked above each other with different conductivity has also already been known from the U.S. Pat. No. 3,370,466. Several pairs of electrodes are disposed in a measuring vessel in each case at the same height distance, to which a d-c voltage is cyclically applied. The liquid limit to be determined is between successive pairs of electrodes between which a jump in the electrical conductivity is determined.

A measuring system for measuring the liquid height in a cylinder is also already known from the U.S. Pat. No. 4,450,722, in which red/green light sources and red/green light sensors are disposed in each case at the same height distances above each other at opposite sides of the transparent measuring cylinder. The red portion of the light is absorbed in such measuring paths which are below the water level so that only the green sensors respond and produce a green signal. On the other hand both a green and a red signal is produced in such measuring paths which are above this height level of the water level. The occurrence or disappearance of the red signal shows indicates that there must be the water level between these height levels.

From the DE-OS 16 07 007 and 16 32 938 devices for milk quantity measurement area also already known, in which the obtained milk is in each case sprayed in one jet vertically from below against a concave baffle screen so that a milk liquid screen reaching across 360° results. The milk flowing off across a certain angular range of this screen is collected and supplied to a measuring cylinder. The height of the milk level in this measuring cylinder is read with the eye and represents practically the share of the total amount of milk which corresponds to the ratio of the angular range on which the milk is collected to 360°.

From the GB-PS 1 316 573, the DE-AS 28 10 376 and the EP 0 057 267 milk quantity measuring devices are also already known which measure intermittently batchwise. The obtained milk is introduced into a measuring vessel until a floater floating on the milk or a sensor located at a predetermined height emits a signal due to the milk level reaching this sensor. Then the supply of further milk is interrupted while at the same time an overflow valve is opened at the measuring vessel from which the entire milk can flow off or the milk can flow off as long as a sensor located at a lower level emits a further signal whereupon the milk overflow valve is closed again and the inflow of obtained milk accumulated in the meantime is released into the measuring vessel. Since the volume between the sensor located at the upper height level or the second senor located at the lower height level is known, the total quantity of milk can be determined by adding up the individual batches assuming that the milk has a constant specific density.

A milk flow meter is also already known from the DE-OS 32 10 465, in which the obtained milk is introduced into a retaining vessel which has an outlet with a predetermined cross-section at its lower end. In this arrangement the retaining height of the milk is to be detected capacitively by means of electrodes disposed at the inner walls of the retaining vessel to determine the respective milk flow of the milk flowing off in connection with the cross section of the outlet line.

A similar device of a milk flow meter is also already known from the U.S. Pat. No. 4,452,176 in which the obtained milk also flows into a retaining vessel from which it flows off via a vertical measuring slot. Also here the retaining height is to be determined from a capacitance measurement to determine the milk flow. A problem common to both devices resides in that due to the mixing of the milk with air the retaining height cannot be unequivocally determined by means of a capacitive measurement and, on the other hand, the milk flown off via the outlet cross-section can likewise not be unequivocally determined, because the specific density of the milk flowing off is changed in broad limits.

The problem of milk quantity measurement which has so far only insufficiently been taken into account resides in that milk is a very foaming fluid so that in the case of the volume measuring processing the measurement is falsified by the foam or the air portion so that the mass can no longer be unequivocally inferred from the volume as this is for instance possible to a very great degree in the case of water.

First of all milk gases, in particular carbon dioxide and nitrogen, are bonded in the milk which vary approximately between three and nine per cent by volume. The by far still greater gas portion is however caused by the admixing of air, in particular during the milking process. An air/milk mixture is produced in the milking machine for transporting the milk through an air inlet in the milking equipment, which contains approximately between 30 and 1 per cent by volume of milk depending upon the milking conditions. In order to eliminate the air from the milk a degassing path or a degassing vessel with less turbulence and sufficient surface is needed. While large gas bubbles, approximately with a diameter of 3 mm, rise relatively rapidly, with an end speed of approximately 300 mm/s, small bubbles, e.g. with a diameter of 0.3 mm take approximately ten times longer. The measuring problem in the volume measurement of milk is thus mainly caused by the small milk bubbles which account for approximately 10 to 15% of the milk volume.

These small bubbles cannot be satisfactorily removed from the milk with mechanical separating means such as inlet cyclone, filling of the measuring chamber from below, etc. in particular not in small milk quantity measuring devices suited for the mobile use on the farm with correspondingly short milk residence times.

The air portion and the bubble size are however not always the same, but depend on a plurality of factors which cause a different foam formation. Such factors are for instance the milk flow quantity, the guiding of the milk tube, the type of the milking system, the type of teat rubber, the diameter of the milking tube, the type of the milking system, the feeding of the cows which changes the milk composition, the health of the udders, the differences between the individual cows and differences in each individual cow due to the lactation phase.

Due to these given factors it is practically impossible to estimate for instance a height in a milk vessel, of which it is assumed that the volume below this height consists of pure milk, while the foam located above this height is neglected as no longer containing any essential milk share. That is to say that the attempt of getting the foam share under control by a corresponding general calibration of the level measurement is doomed to failure, in particular in small vessels as they are above all necessary for mobile milk quantity meters. The air portion of the accumulated fluid is not rarely 30 per cent by volume and more in such vessel sizes. And even in large-volume milk quantity measuring devices, socalled recorders, the white horse may contain between 0 and 0.5 kg depending upon foam height and foam consistency which can account for approx. 5% in a typical milking output of for instance 10 kg per milking process. Recorders are customarily read at the boundary layer milk/foam, i.e. one does not evaluate the amount of milk in the foam because one does not know the foam consistency.

A device for the monitoring or measurement of the foam level in a flotation concentration system is already known from the DE-OS 27 20 006. Several electrode rods are provided in this arrangement which are disposed in vertical arrangement in parallel to each other and project with their lower end against the surface of the liquid to a differently great degree. As soon as the foam contacts an electrode upon a rising of the foam, an electrical circuit is closed due to the conductivity of the foam. Thus the height of the foam is on the whole indicated by the number of the closed circuits of the individual electrodes. The height indication is also effected here due to a yes/no indication of the individual electrode circuits.

Above reference was made in each case to milk as a foaming liquid. However, all other foaming liquids such as in particular beer or fruit juices or other technical foaming liquids such as galvanizing liquids have the same problems as milk.

The present invention is based on the object to determine the foam profile of a foaming liquid, i.e. to determine the specific density of the liquid/air mixture as a function of the height.

This is achieved according to the invention starting from a measuring process of the type mentioned at the beginning by measuring a reference measuring value ($I_O$) for the measurement of the specific density of the foaming liquid at different height levels on a reference measuring path containing substantially degassed liquid, that as a function of the fact whether a measuring value ($I_L$) measured in air is greater or smaller than the reference measuring value ($I_O$) obtained on the reference measuring path a ratio value ($c_m$) according to the ratio from the reference measuring value ($I_O$) and the measuring value at this height level ($I_m$) or the reciprocal value of this ratio is formed for each height level, that possibly in accordance with a preceding calibration a corrected ratio figure ($c'_m$) which is equal to 1 for the deaerated liquid and substantially equal to zero for air is formed and that each ratio value ($c_m$, $c'_m$) is multiplied by the value for the specific density ($\rho$) of the degassed liquid.

The process according to the invention provides the prerequisite of determining the mass of a foaming liquid due to a volume measurement by being able to determine the share of the respective liquid at each height of the liquid/air mixture. It can be achieved that by a suited selection of the parameters of the measuring device the measured ratio values $c_m$ are equal to the desired facts, which indicate the specific density at the respective height level by a multiplication by $\rho$. Possibly a calibration according to a process indicated below must be carried out once in order to thus obtain corrected ratio values $c'_m$ by means of a correction.

Advantageously the mass of the liquid contained in a vessel can be determined by determining the ratio value ($c'_m$) at each height level (m), that the volume ($V_m$) being located between a height level and the next lower height level or the bottom of the vessel is determined in each case, that in each case the product ($c'_m \times V_m$) from the volume ($V_m$) located below a height level, the ratio value ($c'_m$) determined for this height level and the specific density of the milk ($\rho$) is formed in each case and that for determining the entire liquid mass (G) the sum of all products thus formed is formed across all height levels (n) in accordance with $$G = \sum_{m=1}^{n} c'_m \times V_m \times \rho$$

Thus a process is provided according to the invention in which the entire measuring volume is subdivided into layers and in which a specific density of the milk/air mixture is determined for each layer by measuring the ratio value, which represents the instantaneously present milk/air ratio. Thus the milk mass contained in the foam can for the first time be detected in a volume measurement and taken into account in the determination of the total milk mass.

Starting from the aforementioned equation for the total mass it becomes readily apparent that under certain prerequisites the formation and processing of the individual measuring values can also be carried out in another fashion to reduce the necessary time for each total measurement. If one proceeds from the assumption that the volume $V_m$ is constant $= V_0$ at each height level and that each calibrated ratio value $c'_m$ is represented by $$\frac{\Gamma_m}{\Gamma_0},$$

wherein $\Gamma'_m$ means the calibrated measuring value for the height level m and $\Gamma'_0$ means the calibrated reference value, then the aforementioned equation can be simplified to $$G = \frac{V_0 \cdot \rho}{\Gamma_0} \cdot \sum_{m=1}^{n} \Gamma_m = \frac{n \cdot V_0 \cdot \rho}{\Gamma_0} \cdot \frac{1}{n} \cdot \sum_{m=1}^{n} \Gamma_m$$

Because $\dfrac{V_0 \cdot \rho}{\Gamma_0}$ is constant, the measurement would be reduced to an adding up of the calibrated measuring values $\Gamma'_m$ and a multiplication by the factor $$\frac{V_0 \cdot \rho}{\Gamma_0}$$

If, on the other hand, one considers that n. is the total volume V across all height levels and that $$\frac{\Gamma_1 + \Gamma_2 + \ldots \Gamma_n}{n \cdot \Gamma_0}$$

can be considered as a calibrated ratio value $\bar{c'}$ and can be averaged by means of via n, the mass G can be determined from $$G = V \cdot \rho \cdot \bar{c'}.$$

It is evident that also in this case the ratio $$\frac{\Gamma_m}{\Gamma_0} \quad (m = 1, \ldots, n)$$

must not be formed at first in each case, but that at first the sum $$\sum_{m=1}^{n} \Gamma_m$$

may be formed.

In order to simplify the measurement as described above by selecting an equal volume $V_O$ at each height level, a cylindrical vessel with optional base area is preferably used and the height levels are provided at equal mutual height distances. However, the same volumes $V_O$ could of course also be achieved with irregular vessel cross-sections if the electrodes are disposed in corresponding different height distances which are adapted to the cross-sectional shape.

The reference measurement should be carried out in the same milk which is also collected in the actual measurement to avoid that there are any differences due to another milk consistency, etc. This reference measurement can be carried outside the actual milk vessel and it should only be ensured that the milk is deaerated to a very large degree, that is to say, that it practically no longer contains any air bubbles. Since however a reference measuring path outside the milk measuring vessel again renders the measurement altogether more difficult, the reference measurement is preferably carried out at the bottom of the vessel itself. It is proceeded from the experience here that in the case of the measurements in question milk has already accumulated up to a certain height before the measurement is carried out. Under these conditions the milk located near the bottom is already largely deaerated in the case of a suited dimensioning of the vessel.

It became apparent that the measurements can fundamentally be carried out with different methods using different parameters of the milk. Such measurements are especially suited for this, in which the measuring value which results for deaerated milk differs by at least one magnitude from the measuring value measured for air. The ratio value is then formed from these values in such fashion that for the ratio of the measuring value for air in relation to the reference measuring value or by formation of the reciprocal value a ratio value substantially smaller than 1 results, while for the ratio of the measuring value for the deaerated milk in relation to the reference measuring value the value 1 results in each case automatically.

Measurements of this type can be carried out using the properties of the milk such as the electrical conductivity, the thermal conductivity or the infrared absorbing power, which vary very strongly as a function of the milk/air ratio. The resistance of the measuring path can serve as a measuring magnitude using the change of the electrical conductivity of the milk, the amount of light transmitted can serve as a measuring magnitude using the IR absorption or the voltage drop at a temperature sensor can serve as a measuring magnitude using the thermal conductivity of the milk.

According to a preferred embodiment of the invention deviations of the individual measuring paths resulting due to changes or soilings of the individual electrodes or measuring paths can be compensated by carrying out the same measurements at all height levels using the same calibration liquid such as water. A mean value is formed from the resultant measurements including the measurement on the reference measuring path and the deviations of the individual measuring paths from this mean value are taken into account with a corresponding correction factor for the actual measurement.

It is possible to select the parameters of the measuring device suitably in such fashion that the measured ratio figure $c_m$ does no longer require any correction. However, in general it is necessary to calibrate a construction type of measuring device once before the actual measurements. Due to this the actually measured ratio value $c_m$ is corrected in accordance with the specific density of the milk/air ratio. As became apparent this can be effected in a simple case by exponentiating, that is, raising to a higher power, the measured ratio values $c_m$ in each case with an exponent greater than zero to form corrected ratio values $c'_m$. If the exponent in such a case has been determined once by a calibration it remains unchanged for all later measurements.

According to the invention a process for the measurement of the flow of a foaming liquid, in particular for the measurement of the flow of milk mixed with air is indicated, in which a measuring value depending on the same parameter of the liquid contained in a vessel is measured in each case at several different height levels and which distinguishes itself by the fact that liquid is supplied to the vessel, that liquid flows off continuously via a substantially vertical measuring slot, that a reference measuring value ($I_O$) is measured on a reference measuring path containing substantially degassed liquid, that as a function of the fact whether the measuring value ($I_L$) measured across a corresponding measuring path in air is greater or smaller than the reference measuring value, a ratio value ($c_m$) in accordance with the ratio of reference measuring value ($I_O$) to the measuring value at the respective height level ($I_m$) or in accordance with the reciprocal value of this ratio is formed for each height level (m) and that the quantity of liquid flowing off through the measuring slot per time unit is determined from the equation $$m_{eff} = \left( K \cdot \sum_{m=1}^{n} \sqrt{c'_m \sum_{i=m}^{n} c'_i} \right) \left( 1 - a \sqrt{K \sum_{m=1}^{n} \sqrt{c'_m \sum_{i=m}^{n} c'_i}} \right)$$

wherein $m_{eff} \left[ \frac{g}{sec} \right]$ = total mass flow leaving the slot $K = d \times s \times \rho \sqrt{2\, gd}$ d [cm] = distance of electrodes = distance of height levels $g \left[ \frac{cm}{sec^2} \right] = 981 \frac{cm}{sec^2}$ s [cm] = slot width $\rho \left[ \frac{g}{cm^3} \right]$ = specific density of the liquid n = total number of electrodes
$c'_m$ = formed ratio figure between 1 and 0 at the height level m
a = constant of the measuring device depending on slot width, slot edge, etc., which can be ascertained by calibration.

The process can also be used to determine the total mass of the flown liquid by a subsequent summation or integration of all measured flows.

The formula results by a derivation from the socalled Bernoilli's equation by calculating the outflow rate of the liquid/air mixture resulting due to the hydrostatic pressure in a height level for each height of the slot taking a vertical slot as a basis for each height of the slot and a customary correction for the outflow behaviour of a fluid at a slot is taken in account as a function of the speed, with which the hydrostatic pressure at a certain height level can be computed from the measured foam profile and the specific density at this height level is also determined by means of a measurement. The flowing out at a vertical slot represents of course only a special case which is not to restrict the inventive idea. The flow of a foaming liquid can likewise be computed for instance also by a simple computation, which flows off for instance through an opening provided at the bottom of the vessel since the hydrostatic pressure of this liquid at the flow outlet can be determined by measurements of the respective liquid portion at the different heights.

According to the invention a device for the measurement of the specific density of a foaming liquid, in particular of a milk/air mixture is indicated comprising a vessel and at least one measuring device with which a measuring value can be measured in each case depending on the same parameter of the liquid contained in the vessel at several different height levels of the vessel, which is distinguished by the fact that a reference measuring path containing substantially deaerated liquid is provided, that a device is provided which forms a ratio value ($c_m$) corresponding to the ratio from the reference measuring value and the measuring value at this height level or in accordance with the reciprocal value of this ratio for each height level as a function of the fact whether a corresponding measuring value ($I_L$) measured in air is greater or smaller than the reference measuring value ($I_O$) obtained on the reference measuring path, that a corrected ratio figure ($c'_m$) which is equal to 1 for the degassed liquid and substantially equal to zero for air is possibly formed in the device in accordance with a preceding calibration and that a multiplication element is provided with which each ratio value ($c_m$; $c'_m$) is multiplied by the value for the specific density ($\rho$) of the degassed liquid.

Such a device can be suitably used in a device for measuring the liquid quantity, which is distinguished by the fact that a computing means (MP) is provided which multiplies the ratio figure ($c'_m$) determined for each height level (m) by the size of the volume ($V_m$) in the vessel enclosed between this height level and the height level located thereunder and the specific density of the degassed liquid ($\rho$) so that the product $c'_m \times V_m \times \rho$ is formed and that an adding means is provided for adding the products formed for all height levels to indicate the total quantity of liquid (G) as $$G = \sum_{m=1}^{n} c'_m \times V_m \times \rho$$

For the measurement of milk a device has proved to be especially suited, in which an electrode is disposed at the vessel at each height level and a joint counter-electrode facing all electrodes is provided. Using the change of the electrical conductivity of the milk as a function of the milk/air mixture the electric resistance on each measuring path, i.e. between an electrode and the counter-electrode is preferably measured.

For this purpose an a-c voltage is preferably used to avoid polarisations. Moreover a decoupling capacitor is suitably switched between the voltage source and the joint counter-electrode to eliminate any d-c portion. The frequency should preferably be between 200 Hz and 80 kHz and more preferably be 2 kHz to improve the switching on behaviour and to avoid time-dependent drift phenomena.

In view of the air bubble size occurring with preference in milk, electrodes are used here which are substantially circular and have a diameter ranging from about 0.5 to 1.2 mm. In fine optimizing a stronger dependence on small air bubbles was detected for the larger diameter of this range and a stronger dependence on large air bubbles was detected for small electrodes of this range. In order to achieve a dependence being as uniform as possible, an electrode diameter of 0.8 mm is preferably used.

The mutual height distance of the electrodes from each other was preferably in a range of 1 to 8 mm. Especially advantageous results were achieved at a height distance of 1.5 mm. The smaller the distance between electrode and counter-electrode was, the stronger was the change of the ratio value as a function of the respective measuring value. Therefore electrode distances between 2 and 150 mm and more preferably between 3 to 8 mm were used.

In the embodiments in which the ratio values are formed from measuring values of the electrical conductivity of milk it became apparent that the corrections of the measured ratio values necessary due to a calibration could be achieved by exponentiating with the same figure greater than zero.

According to a further preferably used quantity measuring device an IR light source and a mirror arrangement are provided by means of which the IR light ray can be radiated successively at different height levels through the milk contained in the vessel and an electrooptical transducer common to all height levels or an electrooptical transducer for each height level are provided which generates an electrical measuring value signal corresponding to the received luminous intensity.

A further quantity measuring device using the change of the thermal conductivity of a milk/air mixture distinguishes itself by PTC temperature sensors disposed at the milk vessel at different height levels, by constant-current sources, which supply in each case a constant heating capacity to the PTC temperature sensors and by resistance measuring circuits which determine the resistance value corresponding to the temperature of a PTC temperature sensor as a measuring value.

BRIEF DESCRIPTION OF THE DRAWINGS

In the following the invention will be described by means of embodiments represented in the drawing. For the sake of simplicity the embodiments only refer to measurements of milk. However it must be clarified that the invention can also be used for every other foaming liquid.

DETAILED DESCRIPTION

Figure 1:
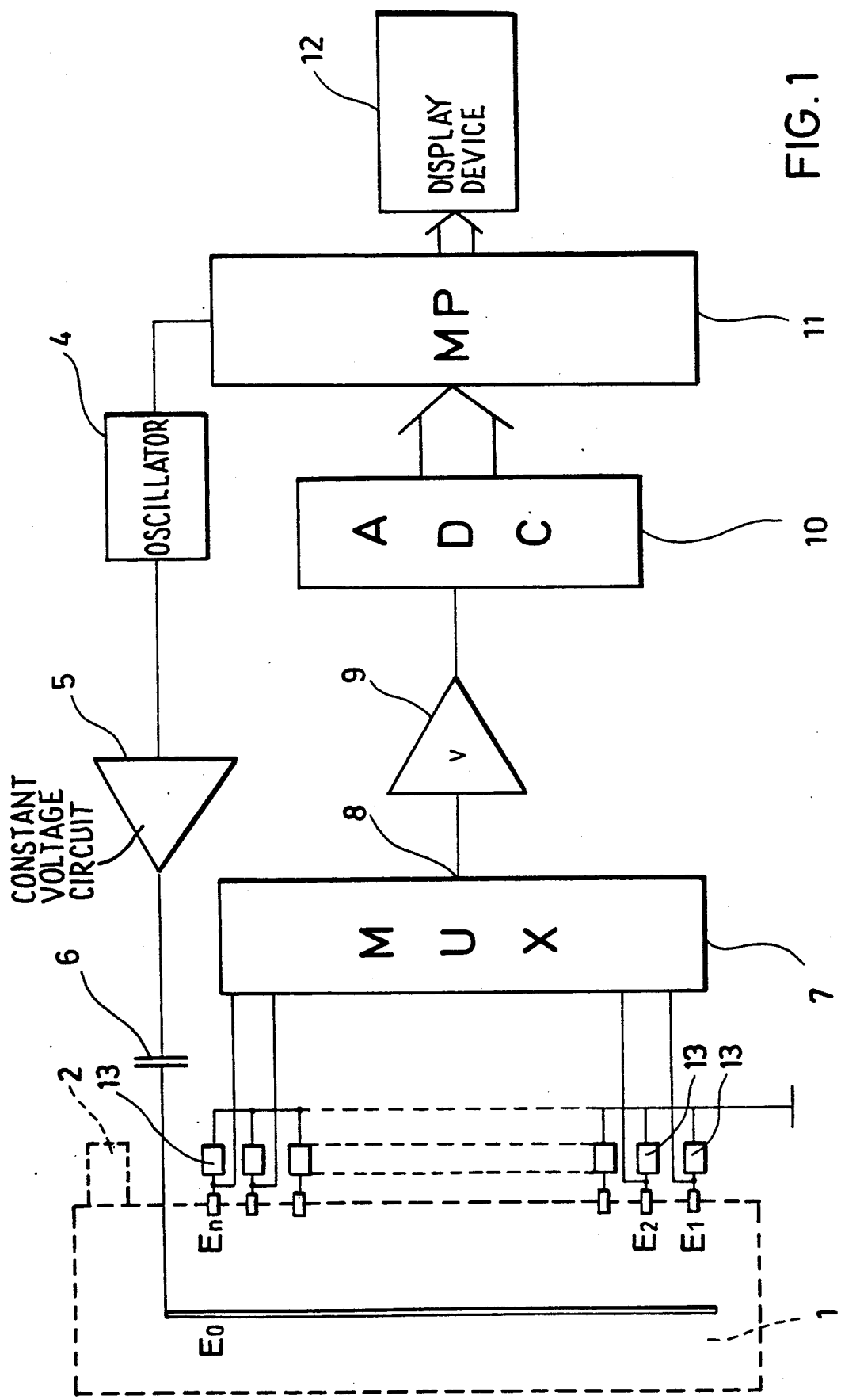
FIG. 1 shows schematically a first embodiment of the invention for the measurement of the electric resistance of a milk/air measuring path and the associated circuit.

A vessel 1 is schematically represented in FIG. 1, in which milk is supplied continuously or discontinuously via an upper inlet 2. Several individual electrodes E1 to En being electrically insulated from each other are disposed at the inner side of the vessel 1 at equal height distances. These electrodes may also be guided through the wall of the vessel. The electrodes need not be disposed vertically above each other, but may also be disposed on a helical line or disposed above each other in lateral staggered relationship. A joint counter-electrode $E_0$ is disposed in the vessel which is opposite to all electrodes and disposed at equal distance from them. Voltage is supplied to the counter-electrode $E_0$ by an oscillator 4 via a constant-voltage circuit 5 and a decoupling capacitor 6. The voltage is preferably a sine-wave a-c voltage, however a triangular a-c voltage could also be used. The electrodes $E_1$ to $E_n$ are connected to mass in each case via resistors 13. The connection points between the individual electrodes $E_1$ to $E_n$ and their resistors 13 being in series with this are in each case (analogously) connected to a multiplexer 7. The output 8 of the multiplexer 7 is connected to analog-to-digital converter 10 via an active rectifier 9. The same supplies the measuring values to a microprocessor 11, which is in turn coupled to the oscillator 4. A display means 12 or a printer is connected to the output of the microprocessor 11.

The size of the vessel 1 depends of course on the milk quantity to be altogether measured. The diameter or the cross-section of the vessel must be selected accordingly. Since according to the invention the ratios of the specific density of the milk are judged sectionwise in superimposed layers, the volume of each layer depends of course both on the cross-section of the vessel and on the mutual height distance of the individual electrodes $E_1$ to $E_n$. For the sake of simplification a cylindrical vessel and a constant height level difference was selected. The height distance of the electrodes from each other was 1.5 mm. The electrodes consisted of electrodes with circular cross-section which had a diameter of 0.8 mm. As already stated at the beginning the bubbles forming in the milk have a different diameter. The part of the milk having large air bubbles is deaerated or degassed relatively quickly and moreover the share of the milk contained in a foam with large bubbles is relatively small. The share of the milk in which smaller bubbles are contained is on the other hand degassed substantially more slowly and the share of the milk in this milk/air mixture, i.e. this foam, is substantially higher. It was found that in the case of the use of electrodes with a diameter greater than 0.8 mm a strong dependence of the measuring values on very small bubbles was obtained, while the average-size or large bubbles practically did not show any detectable influence in the form of a noticeable change of the measuring value. On the other hand, electrodes with increasingly smaller diameter than 0.8 mm showed an increased response to bubbles with relatively large diameter, while small and average-size air bubbles only showed a small change of the measuring value. For this reason a mean value of 0.8 mm was preferably selected for the electrode diameter, for which both a dependence on small and on large bubbles can be detected.

The working method of the measuring device shown in FIG. 1 is the following one:

An a-c voltage is applied to the counter-electrode $E_0$ by the oscillator 4. A frequency of 2 kHz is preferably used. In the case of substantially greater frequencies of approximately 20 to 80 kHz a better, namely shortened transient behaviour was observed, however the obtained measuring signals became smaller. On the other hand, the obtained measuring signals were greater at frequencies substantially lower than 200 Hz, however here a long transient behaviour and possibly even a drift lasting for a longer period of time were observed. Therefore it was preferably worked in continuous operation.

A lower limit for the lower frequency was also set due to the fact that the total number n of the electrodes is to be scanned if possible in a total time of less than about 0.5 sec. Finally an a-c voltage was used to eliminate any polarisation phenomena. For this reason a decoupling capacitor 6 is used downstream of the constant voltage amplifier 5 which suppresses any d-c voltage portions.

The measuring path only forms one ohmic resistance. All electrodes are operated in equal-phase fashion. A phase shifting resulting due to the decoupling capacitor has an equal effect for all electrodes due to the switching of the decoupling capacitor between oscillator and joint counter-electrode.

Due to the substantially higher conductivity of milk as compared with the conductivity of air there is a substantially higher measuring value signal at the electrodes between which there is already milk than at those electrodes between which practically only air is present. The measuring value signal results for each electrode $E_m$ at its associated resistor 13 in the form of a corresponding voltage drop. These measuring value signals occurring at the individual electrodes $E_1$ to $E_n$ are then successively scanned one after the other in terms of time by the multiplexer 7 and transmitted to the analog-to-digital transducer 10 via an amplifying rectifier, which then transmits corespondingly digital output signals to the microprocessor 1. The scanning of all electrodes by the multiplexer is preferably effected in a total time being shorter and possibly substantially shorter than the time difference between milk surges arriving successively. If the teats of a cow are milked one after the other, this time difference is approximately 0.5 seconds. A suitable total scanning time is in this case 0.1 seconds.

The microprocessor has at first the task of forming the ratio value $c_m$. For this purpose it stores at first the measuring value on a reference measuring path. As already stated above the measuring value is preferably used as reference measuring path, which is measured at the lowermost height level, i.e. the height level directly above the bottom of the measuring vessel 1. Here it is proceeded from the fact that the milk which is directly above the bottom of the vessel is practically already completely degassed. In the present case the measuring value which is measured by the lowermost electrode, i.e. the electrode $E_1$, is used as a reference value. If the resistance $R_m$ is measured as a measuring value, which results in each case on a measuring path m between one electrode and the counter-electrode, the measuring value $R_1$ forms the reference value $R_0$ for the electrode $E_1$. Since the resistance is greater in pure air than under the same measuring conditions in degassed milk, the ratio $$\frac{R_O}{R_m} = c_m$$

is formed as ratio value $c_m$ for each electrode $E_m$. If the conditions for all measuring paths and the reference measuring path are equal, the values of the ratio value $c_m$ are between 1, which would correspond to practically degassed milk, and the value 0, which would practically correspond to a measuring path in air.

Figure 2:
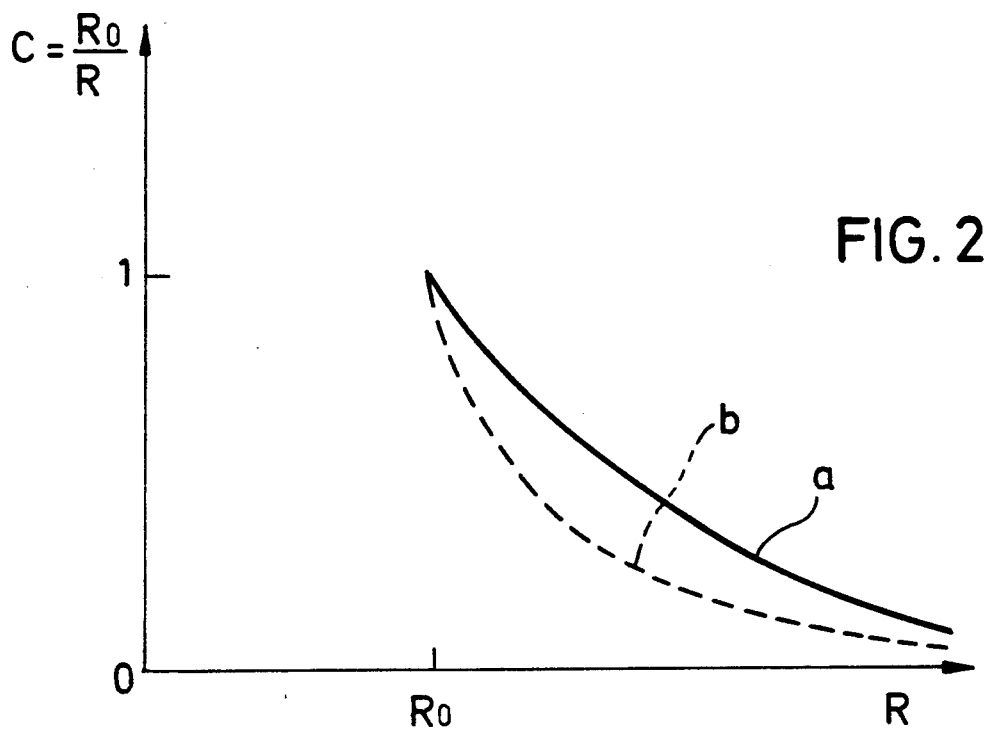
FIG. 2 shows a diagram to explain the ratio value.

The dependence of the ratio figure $$c = \frac{R_O}{R}$$

on the size of the measuring value R is for instance represented in FIG. 2. It is pointed out that c is the ratio value measured at one height level by which the specific density $\rho$ of the degassed milk is multiplied to determine the specific density of the foam at this height level. As was detected the course of this hyperbola curve also depends on the distance between the electrodes and the counter-electrode. The course of the curve corresponds approximately to the curve a in the case of large electrode distances or measuring paths, in which, however, the usable signals are relatively small, whereas in the case of small electrode distances a course corresponding to curve b results approximately, i.e. the course of the hyperbola is steeper. As can be seen the two different curves represent different evaluations of the share of milk in the foam or likewise a different evaluation of air in the respective foam. Prior to the use of every measuring device it is generally customary to calibrate it. Accordingly a certain calibration must therefore be carried out approximately by comparing the calculated milk mass G with the milk mass determined by weight for every measuring arrangement prior to its use to correct the respectively measured ratio value c in accordance with the calibration.

In general a calibration can approximately be carried out in the following fashion: A sample of the measuring vessels to be calibrated and being of the same construction is first of all weighed in empty condition with the measuring sensors contained in it, then filled with foaming milk and the ratio value $c_m$ for each height level m is formed from the measuring value $I_m$ and $I_O$. Then weighing is carried out again to determine the mass G of the foaming milk filled into it. This process is repeated 50 to 100 times with foaming milk being different, if possible, from different cows under possibly different milking conditions.

The formed ratio values $c_m$ are first of all transformed by means of a mathematical search process known per se to correct ratio values $c'_m$ from the data material obtained in this fashion so that the following equation is complied with for all calibration measurements (weighings) carried out:

$$G = \rho \times \sum_{m=1}^{n} V_m \times c_m$$

wherein
$c'_m = \bar{a} + \bar{b} \times c_m + \bar{d} \times c^z_m$ and
$0 \leq c'_m \leq 1$.

The coefficients $\bar{a}$, $\bar{b}$, $\bar{d}$, z of this general regression statement can be stepwise approached to the true coefficient values searched for by means of the stepwise regression analysis. In this mathematical method the minimizing of the sum of the squared deviations between the respectively weight and calculated mass of the milk is the decision criterion for the degree of the approximation.

If the ratio values $c_m$ formed from the measurements are already between zero and 1, it is mostly sufficient to set $\bar{a} = \bar{b} = 0$ and $\bar{d} = 1$ and to only vary z. The value for z which results in these cases from the regression analysis is between approximartly 0.33 and 3.

According to the same principle the calibration of the flow meters which will be explained below can be effected. The mass flow to be ascertained can in particular be also ascertained by weighing (and differentiation) via a weighing vessel connected downstream. The weighing vessel is weighed at successive times. The time delay must of course be taken into consideration here, which results between the respective measurement at the electrodes in the measuring vessel and the flowing in of the milk/foam mixture into the weighing vessel.

It was found in the measurement arrangement described by means of FIG. 1 that a correction of the measured ratio value with one and the same exponent could in each case be effected, which is between 1 and 2 to bring in this fashion the milk mass determined by summation with the milk mass determined by weighing into keeping. In this fashion the corrected, calibrated ratio values $c'$ are obtained. In curve a of FIG. 2 which was measured with an electrode distance of 30 mm all $c_m$ values were exponentiated with an exponent of about 1.6. Whereas in curve b which was measured with an electrode distance of 3 mm all measured $c_m$ values had to be exponentiated with an exponent of about 1.1. (I.e. $(c_m)^z = c'_m$ is in each case formed, z being the exponent determined by the calibration.)

Thus the microprocessor determines an associated ratio value $c'_m$ taking the mathematical correction for each scanning of an electrode $E_m$ into account which is possibly necessary due to the calibration. This ratio figure is multiplied by the normal density $\rho$ of the milk so that one can say that the product $c'_m \times \rho$ results in a specific density modified in accordance with the air share for each height level m. Since in the described embodiment the volume $V_m$ is equal between two successive height levels or electrodes $E_m$ and $E_{m-1}$ approximately equal to V, one obtains by the multiplication of the values $c'_m \times \rho \times V$ the milk mass which is present in the respective height layer. Then the total mass of milk in the vessel 1 results by summing these milk masses for each height level m across all height levels 1 to n. These computing processes are carried out automatically by the microprocessor MP. The total milk mass is then displayed on the display means 12.

Figure 3:
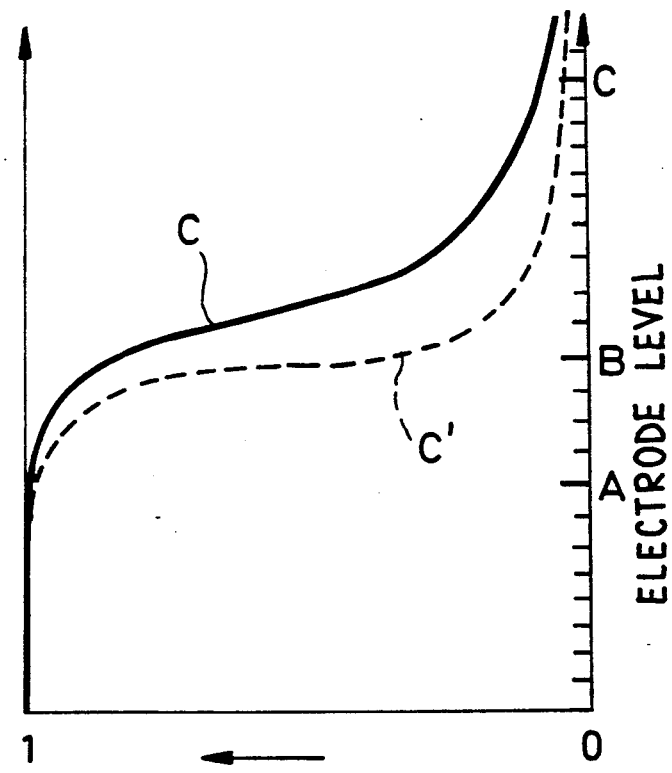
FIG. 3 shows the course of the ratio value c in unbroken line as it was measured by the electrodes of a certain measuring arrangement which are located above each other for a quantity of milk in a vessel at a specific point n time and the course of the ratio value c' in dotted line, which was corrected after calibrated of the measuring arangement.

The dependence of the measuring values of the ratio value c as a function of the height level, i.e. as a function of the superimposed electrodes is recorded in a schematic representation in FIG. 3. The individual markings designate the superimposed electrodes or height levels on the ordinate. The value for the ratio figure C is indicated on the abscissa. In the embodiment described here this value varies already only between 1 and zero. The curve $c'$ shows the ratio values which were in each case obtained from the measured ratio values c by exponentiating with a certain exponent. For curve $c'$ 1 means milk without air, while the value zero indicates air without milk. The representation shows that all electrodes result practically in the measuring value $c' = 1$ up to the height level A, which means that practically air-free milk is present up to this height. The value $c'$ begins to deviate from 1 in the area between the height levels A and B, which means that in this layer milk mixed with air is already present in this layer. Above this height level B the share of air increases to a great extent and above the level C the share of the milk is practically no longer measurable, i.e. insignificant.

The measuring process according to the invention makes not only the measurement of the milk mass in a collecting vessel possible, but also the measurement of the respective milk flow and the determination of the total milk mass from the milk flow measured over the period of time.

So far there has been the following problem in the batchwise milk flow meters already mentioned at the beginning, in which the milk level is determined in each case upon the flowing in of the milk into a milk chamber by a first measuring electrode and upon the flowing out of the milk from the milk chamber by a second measuring electrode. The smaller the volume is which is delimited by the level of the first electrode and the level of the second electrode, the more accurately is the total quantity measurement on principle, because a milk rest remaining at the end of the milking cycle which is no longer sufficient to actuate the electrode located at the higher level is no longer taken into account. If the volume between the two electrode levels has a size of e.g. 200 $cm^3$, this means an error possibility of 200 $cm^3$. However, if a smaller volume for the milk to be carried off batchwise is selected, the control element must be switched more often. (The control elements must e.g. already be switched every 2 seconds e.g. in a milk flow of 6000 $cm^3$/min. and a volume of 200 $cm^3$/batch). However this means that the residence time and thus the degassing time of the milk becomes increasingly shorter in the measuring chamber with the batch volume becoming smaller and thus the measurement becomes increasingly more inaccurate due to the disturbing air share. This disadvantage can be completely eliminated by the process according to the invention.

Figure 4:
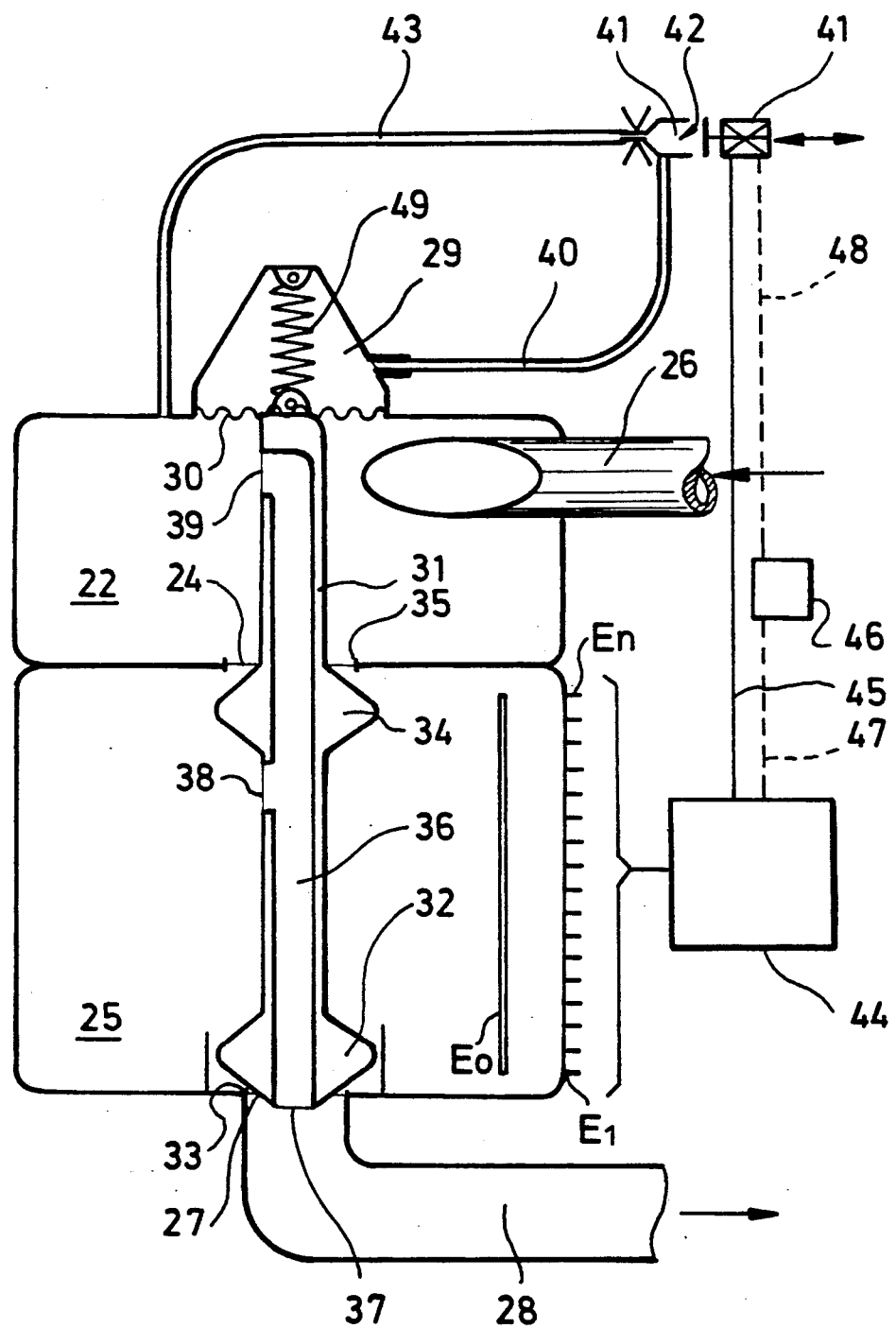
FIG. 4 shows schematically a device for the batch-wise measurement of quantities of milk using the process according to the invention.

An embodiment of a milk quantity measuring device is shown in FIG. 4, in which the milk is measured batchwise. The device 20 comprises a housing 21 which limits an upper inlet chamber 22, which is delimited from the measuring chamber 24 located thereunder via a partition wall 23 with an overflow opening 24 formed therein. The obtained milk being under the milking vacuum gets into the inlet chamber 22 via a feed pipe 26 opening tangentially into the inlet chamber 22. The milk flows off out of the measuring chamber 25 into a milk transport line 28 via a discharge opening at the bottom of the milking chamber 25.

A control housing 29 is mounted on the upper side 21. The inlet chamber 22 adjoins the inner chamber of the control housing 29 via a membrane 30. A piston 31 is fastened to the membrane 30 which projects downwardly through the inlet chamber into the measuring chamber. The lower end of the piston is designed as a push rod 24 which cooperates with a valve seat 35 formed at the overflow opening 24. The push rods are formed in such fashion at the piston 21 that in a first raised position of the piston the push rod 34 rests against the valve seat 34 and closes the overflow opening 24, while at the same time the push rod 32 is lifted from the valve seat 33 so that the discharge opening 27 is open, while in a lower position of the piston 31 the discharge opening 27 is closed by the push rod 32 and the overflow opening 24 is at the same released by the push rod 34. The piston 31 is furthermore traversed by a passage pipe 36 extending along its longitudinal axis which has a first opening 37 ending below the push rod 32, which has a second opening 38 located at the height of the upper part of the measuring chamber 25 and a third opening 39 opening in the upper part of the inlet chamber.

The control chamber 29 is connected to a solenoid valve via a line 40 which on the one hand has an inlet opening 42 for atmospheric air and on the other hand is connected to the inlet chamber 22 via a line 43. The solenoid valve 41 can be controlled in such fashion that the line 40 is connected to the inlet opening for atmospheric air 42 in a first position, while the line 43 is closed at the same time, while in a second position the inlet opening 42 is closed and a connection is established between the lines 40 and 43.

Measuring electrodes $E_1$ to $E_n$ are disposed in a wall of the measuring chamber 25. A counter-electrode $E_0$ is located at a distance before these electrodes within the measuring chamber 25. Electrodes and counter-electrode are connected with the same measuring circuit as it is shown in FIG. 1 and which is only schematically represented as measuring circuit arrangement 44 in the present representation for the sake of a better clearness. The measuring circuit arrangement can be optionally directly connected to the solenoid valve 41 via the line 45 or instead of this a time control circuit 46 may be provided which keeps the solenoid valve 41 excited or de-excited via the lines 47 and 48 and controls at the same time the measuring circuit arrangement 44 in such fashion that the milk quantity being just present in the measuring chamber is in each case determined.

The device can operate in two different fashions depending upon the fact whether the time control circuit 46 is provided or whether the measuring circuit arrangement 44 is directly connected to the solenoid valve 41: The first working method is as follows:

At the beginning there is a milking vacuum across the milk transport line 28, the passage pipe 36 with its openings 37, 38 and 39 and in the milking chamber and in the inlet chamber 22 and in the milk feed pipe 26. The solenoid valve 41 is in a position in which the line 40 is connected to the atmosphere, while the line 43 is closed. Due to the atmospheric pressure prevailing in the control housing 29 as compared with the partial vacuum prevailing in the inlet chamber 22 the piston 31 is adjusted downwardly into its lowermost position contrary to the force of the tension spring 49 which is disposed in the control housing and exerts an upwardly directed tension force on the membrane 30. The push rod 32 rests against the valve seat 33 in this position and closes the outflow opening 27, while on the other hand the overflow opening 24 is open. The milk introduced from the feed pipe 26 into the inlet chamber 22 flows thus directly into the measuring chamber via the overflow opening 24 and is collected in it. At predetermined time intervals which are selected in such fashion that the measuring chamber is not filled up to the height of the opening 38 a periodic change-over is carried out by the time control circuit 46. Upon the arrival of a first change-over signal the milk quantity located in the measuring chamber 25 at this point in time is automatically determined by the measuring circuit arrangement and the value is stored. The change-over pulse effects at the same time that the solenoid valve 41 is switched over so that now the connection of the line 40 with the atmosphere is interrupted and a connection with the line 43 is at the same time established. Due to this a pressure balance takes place between the inlet chamber 22 and the control housing 29, due to which the membrane 30 with the piston 31 attached to it is upwardly deflected due to the tension spring 49. The piston 31 adopts due to this an uppermost position in which the push rod 34 rests against the valve seat 34 and closes the overflow opening 24. Thus all milk arriving from the feed line 26 is collected in the inlet chamber 22. At the same time the outflow opening 27 is opened by rising the piston so that the milk can flow off out of the measuring chamber 25 via the milk transport line 28.

Due to the passage pipe 36 it is ensured and also during the flowing off of the milk the same pressure prevails both in the milk transport line 28 and in the measuring chamber 25 and in the inlet chamber 22 so that the milk flows off alone due to its own weight. After a predetermined period of time switching over to the original condition is again effected by means of the time control circuit 46. Due to this a signal is at the same time transmitted to the measuring circuit arrangement 44 which detects automatically the residual amount of milk possibly remaining in the measuring chamber 25 at this point in time. This value is also stored in the measuring circuit arrangement 44 and the difference between the first and the second stored value results in the milk quantity actually flown off in a batch. That is to say that the first condition of the solenoid valve and thus also regarding the position of the piston 31 is established by the control pulse from the time control circuit 46 so that now the milk collected in the inlet chamber 22 can flow off into the measuring chamber 25 and is collected there. This process is then repeated until the end of the entire milking process. The measuring circuit arrangement 44 adds the milk mass carried off during each batch at the end and thus ascertains the entire obtained milk mass.

If according to the second working method the solenoid valve 41 is directly connected to the measuring circuit arrangement 44 instead of the time control circuit 46, the working method is similar, however in this case a change-over is not effected periodically after predetermined times, but the measuring circuit arrangement 44 is rather adjusted in such fashion that it measures the milk mass located in the measuring chamber 25 at short time intervals. If a predetermined milk mass is reached, the corresponding change-over signal is then transmitted to the solenoid valve 41 by the measuring circuit arrangement 44. Thus the milk located in the measuring chamber 25 can flow off. Also during this time the milk mass in the measuring chamber 24 is intermittently detected via the measuring circuit arrangement 44. If a predetermined milk mass is fallen short of, the measurement circuit arrangement 44 transmits a renewed change-over signal to the solenoid valve 41. Thus the outflow opening 27 is closed again, while the overflow opening 24 is opened. Also in this case the milk mass flown off per batch is determined from the difference detected by the measuring circuit arrangement 44. These measured milk quantities are added up at the end of the milking process to obtain the total milk quantity.

In this measuring device according to the invention measuring batchwise the advantage is offered as compared with the devices known so far that the batch volume must not always be of equal size. The determination of the change-over time is not effected due to a milk level which cannot be defined in air/milk mixtures, but as a function of either the time or the milk mass actually present in the milk measuring chamber. Also the milk quantity not flown off during each batch is exactly taken into consideration. Finally also the milk masses are taken into account with would possibly no longer be sufficient at the end of the milking process to result in a full batch, for which reason no control or measuring signal would be produced.

Figure 5:
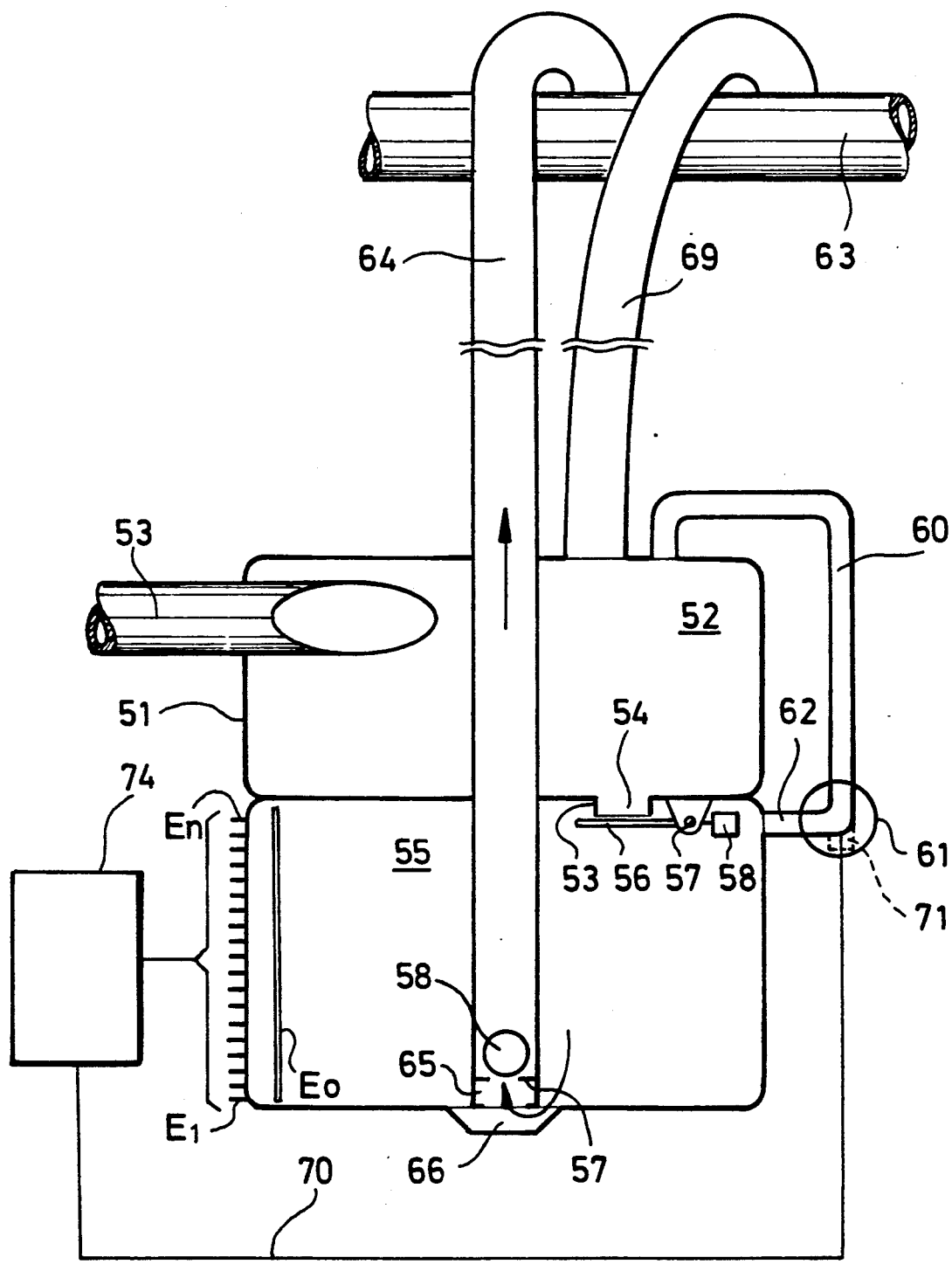
FIG. 5 shows schematically another embodiment of a batchwise milk quantity measurement using the invention.

Another embodiment of a batchwise measuring milk quantity measuring device 50 is shown in FIG. 5. An inlet chamber 52 and a measuring chamber 55 located thereunder and being connected thereto via an overflow opening are provided in the housing 51. The inlet pipe 53 for the milk ends in the inlet chamber. The overflow opening 54 is closed from below by a flap 56, which is designed in the form of a two-arm lever linked at 57 whose second lever arm consists of a counterweight 58 which keeps the flap 56 in abutment and thus in the closing position at a corresponding valve seat 59 at the overflow opening 54.

The inlet chamber 52 is connected to a valve 61 via a line 60 which may consist of a solenoid valve, but which is represented in the form of a ground valve with a plug. The valve itself is connected to the measuring chamber 55 via a line 62.

Moreover the milking line is outlined at 63, via which the milk is carried off by means of a partial vacuum. A pipe 64 projects into the milking line 63 which projects with its other end 65 into a recess 66 in the bottom of the measuring chamber. A nonreturn valve in the form of a ball 58 resting on a valve seat 57 under its own weight is provided in the pipe itself at the end 65.

Finally the inlet chamber 52 is also connected to the milking line 63 via a further line 69.

As already described in the preceding arrangement several measuring electrodes $E_1$ to $E_n$ are provided in the milking chamber, which are disposed opposite to a joint counter-electrode $E_0$. The electrodes are connected to a measuring circuit arrangement 74, which corresponds to the measuring circuit as it is shown in FIG. 1. The measuring circuit arrangement is connected to the valve 61 via an electrical line 70, if it is an electromechanical valve or via an adjusting means (not shown), if it is a mechanical valve.

This device functions as follows:

At the beginning the inlet chamber 52 and the measuring chamber 55 are under the milking vacuum prevailing in the milking line 63 via the line 69 or 64. The milk introduced from the inlet pipe 53 into the inlet chamber opens the flap 56 due to its weight and thus gets into the measuring chamber 55. The measuring circuit arrangement 74 measures at short time intervals the milk mass which is in each case already located in the measuring chamber 55. If a predetermined value is reached for this measured milk mass, a switching pulse is transmitted to the valve 61 via the line 70. The valve which had established a connection between the lines 60 and 62 in its original position is adjusted by this switching pulse in such fashion that the line 60 is closed and the line 62 is connected to an outlet 71 towards the atmosphere. While the inlet chamber 52 is thus still under the milking vacuum, an increase in pressure to atmospheric pressure takes place in the measuring chamber 55. Thus the valve flap 56 is pressed against its valve seat 59 and the overflow opening 54 is thus closed. The milk flowing into the overflow chamber 52 as of this period of time is this collected in it.

The milk in the measuring chamber 55 is at the same time under a difference in pressure, namely on the one hand the atmospheric pressure in the line 62 and on the other hand the milking vacuum still prevailing in the line 64. This leads to that the milk located in the measuring chamber 55 is carried off opening the nonreturn valve 57, 58 via the pipe 64 due to this difference in pressure. During this time the mass of the milk in the measuring chamber 55 is still determined by means of the measuring circuit arrangement 74 at short time intervals. As soon as the complete transport of the milk from the measuring chamber is detected or as soon as the measured milk mass reaches a predetermined lower limit, the measuring circuit arrangement 74 transmits a further control pulse to the valve 61 which resets it into its original position. Due to this a pressure compensation is established in the inlet chamber 52 and the measuring chamber 55 via the now connected lines 60 and 62. In this fashion milk can again flow from the inlet chamber 52 via the valve flap 56 and the process is repeated in the fashion described above.

The nonreturn valve 57, 58 is provided in the pipe 64 to prevent milk in it flowing possibly back from flowing back into the measuring chamber 55.

Figure 6:
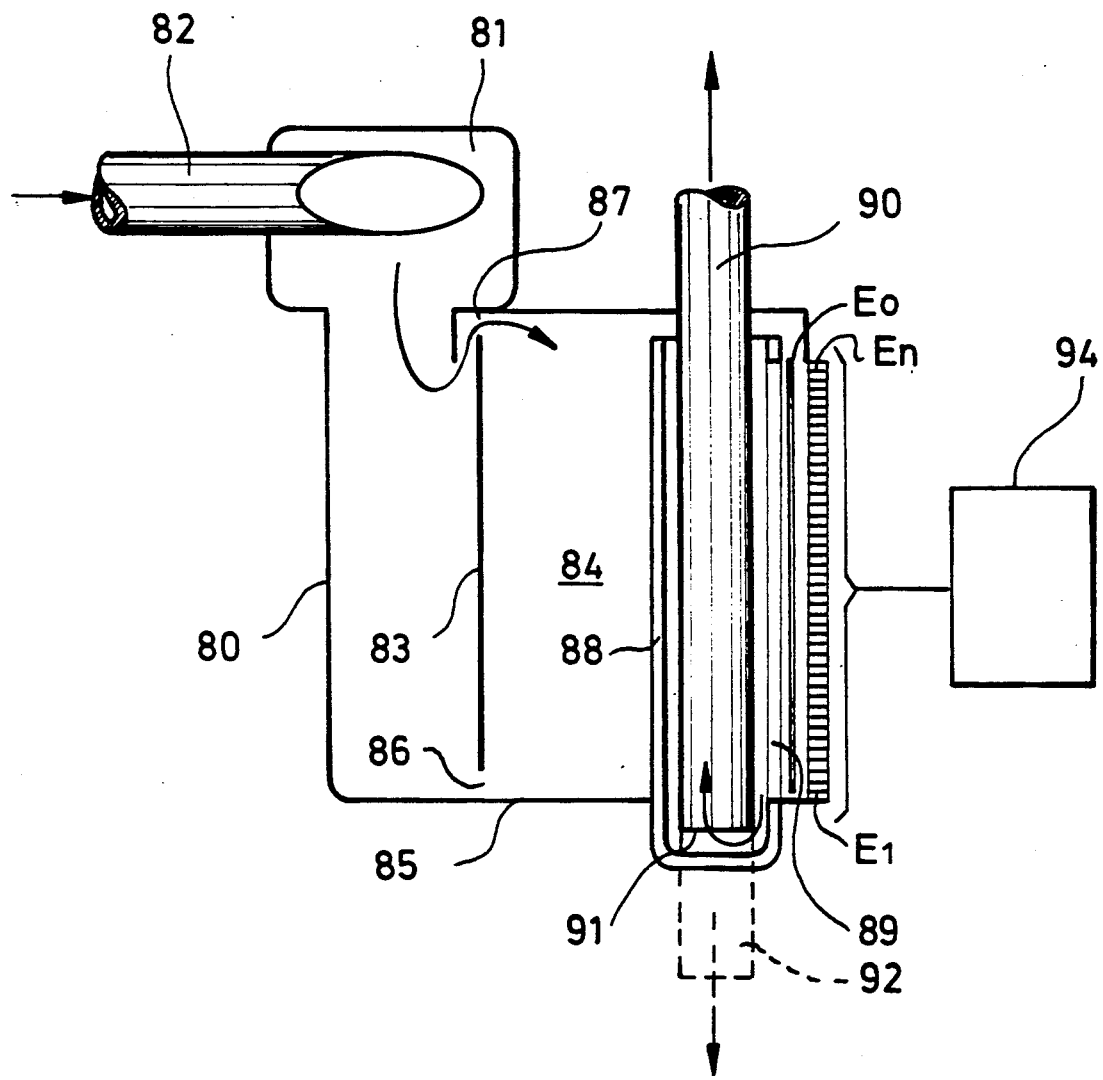
FIG. 6 shows schematically a device for the continuous flow metering using the invention.

An embodiment is shown in FIG. 6 with which the milk flow can be measured practically continuously and by adding up the milk flow curve measured in this fashion the total milk mass can finally be determined over the period of time, which was obtained during a milking process. The device is only schematically represented in order not to divert the attention from the actual subject matter of the invention. An inlet chamber 81 is provided in a joint housing 90 into which the milk is tangentially introduced via an inlet pipe 82 so that the milk is already largely settled. The inlet chamber 81 is separated from the measuring chamber 84 via a partition wall 83. The partition wall 82 has a transfer slot 86 for the milk between its lower side and the bottom 85 of the housing 80 and possibly at the side walls. The restricted transfer of the milk via the slots or via a sieve into the measuring chamber 84 serves for the further settling of the milk. An opening 87 is furthermore provided between the upper end of the partition wall 83 and the housing 80 via which a continuous pressure compensation between the chambers can take place.

A pipe 88 being closed at its lower end and open at its upper end is provided in the measuring chamber 84, which reaches below the bottom 85 of the measuring chamber with its closed lower end. The pipe 88 has a longitudinal slot 89 at its side wall which reaches down to the bottom 85 of the measuring chamber. A further pipe 90 extends coaxially to the tube 88 in the interior of this pipe and at a distance to its inner wall, which is open at its lower end 91. The pipe 90 is connected with its other end to a milking line (not shown) in which the customary milking vacuum prevails. Electrodes $E_1$ to $E_n$ are disposed near the slot 86 at different height levels. A counter-electrode $E_0$ is disposed opposite to these electrodes at a distance thereto. The counter-electrode $E_0$ is preferably mounted on the outer side of the pipe 88, although the counter-electrode is represented in detached fashion in FIG. 6. A measuring circuit arrangement 94 is connected with the electrodes $E_1$ to $E_n$, which corresponds to the circuit as it is represented in FIG. 1.

The longitudinal slot 89 has preferably a constant width s across its entire height. The device functions as follows as a milk flow meter.

The obtained milk reaches the inlet chamber 81 via the inlet pipe 82 and flows downwardly in it. The milk gets into the measuring chamber 84 via the transfer slot 86 and rises in it to the same level as in the inlet chamber 81 due to the pressure compensation via the opening 87. At the same time milk flows off via the longitudinal slot 89 into the interior of the pipe 88 and is carried off from it towards the milking line via the lower end 91 of the pipe 90.

Instead of carrying off the milk upwardly via the pipe 90, the pipe 88 could also be open at its lower end according to another embodiment and be in communication with a milking transport pipe 92 leading downwardly.

At short successive intervals of time ratio values $c_m$ for each height level m or the respective electrode at this height level are now ascertained in each case. Then the effective change of the milk mass per time unit can be calculated according to the following mathematical formula from these ratio values $c_m$ measured in each case at a certain point in time for all height levels 1 to n:

$$m_{eff} = \left( K \cdot \sum_{m=1}^{n} \sqrt{c'_m \sum_{i=m}^{n} c'_i} \right) \left( 1 - a \sqrt{K \sum_{m=1}^{n} \sqrt{c'_m \sum_{i=m}^{n} c'_i}} \right)$$

wherein $m_{eff} \left[ \dfrac{g}{sec} \right]$ = total mass flow leaving the slot $K = d \times s \times \rho \sqrt{2 \, gd}$
d [cm] = distance of electrodes = distance of height levels $g \left[ \dfrac{cm}{sec^2} \right] = 981 \dfrac{cm}{sec^2}$ S [cm] = slot width $\rho \left[ \dfrac{g}{cm^3} \right]$ = specific density of the liquid n = total number of electrodes
$c'_m$ = formed ratio figure between 1 and 0 at the height level m
a = constant of the measuring device depending on slot width, slot edge, etc., which can be ascertained by calibration.

That is to say the respective milk flow can be determined at certain times by programming the microprocessor MP according to FIG. 1 in such fashion that it computes the change of the milk quantity per time unit according to the indicated formula for each measurement of the ratio values $c_m$ and stores it. If one records these values for the milk flow measured at time intervals as a function of the time, one obtains the known milk flow curve during milking. By adding the products of all measured milk flow values multiplied by the length of the time intervals between two successive measurements, the entire acquired milk quantity results.

To calibrate this process the milk acquired actually during the entire milking cycle was weighed as a comparison as in the process which was explained in connection with the embodiment according to FIG. 1 and an adaptation was achieved by a corresponding weighting of the ratio values. It became apparent that the obtained measurements could be brought into a good conformity with the milk quantity determined by the comparative measurement, that the respectively measured ratio values $c_m$ were exponentiated, that is, raised to a higher power, in each case with one and the same exponent between 1 and 2. This calibration must only be carried out once. The parameters then remain constant for all measurements, also with other cows, feeding conditions, etc.

According to one embodiment the cross-section of the vessel in which the milk is accumulated up to a certain height was 35 cm$^2$. The height of the vessel was 12 cm. The individual electrodes had a height distance of about 1.5 mm. A number n=64 electrodes were altogether used one above the other. The distance between the electrodes and the counter-electrode was 3 mm. The width s of the longitudinal slot was 3 mm.

A simplified milk flow measurement can also be carried out by providing a calibrated opening in the bottom of the measuring vessel and that the hydrostatic pressure of the milk above this opening is continuously ascertained by measuring the milk mass above this height level.

As was explained by means of the embodiment according to FIG. 1 a reference measurement is preferably carried out near the bottom of the measuring vessel. The bottom and also the first measuring electrode are normally practically covered with milk directly upon the beginning of the milk flow during a normal milk flow as it occurs at the beginning of the milking cycle. The little air is deaerated relatively quickly. That it to say a reference measuring value is measured practically after a very short period of time, which corresponds to the condition in which the deaerated milk is present. However, there can be the case that an air intrusion occurs due to a badly fitting milking equipment or that at the beginning of a milking cycle more air is contained in the milk than this would correspond to a measurement in deaerated milk. Only in order to guard against these cases the microprocessor is preferably programmed in such fashion that at first a fixed reference measuring value ascertained due to preceding measurements is stored which is used for the initial measurements to form the ratio values $c'_m$. At the same time the arising reference measuring value is measured on the reference measuring path with this and compared to the fixed reference measuring value. As soon as the actually measured reference measuring value reaches at least 85% of the size of the fixedly given reference measuring value, a change-over to the actually measured reference measuring value is carried out for the measurement. Nevertheless the actually measured reference measuring value is still compared with the reference measuring value predetermined fixedly at the beginning. If during the measurement a substantial change of more than 15% of this value should result perhaps due to an air intrusion, an automatic change-over to the fixed reference measuring value is carried out again. It can be achieved in this fashion that a reliable measurement is carried out even if it is worked with extremely unfavourable air/-milk ratios as they occur e.g. in extremely high milk flows, in which the turbulence in the milk caused by air is very intensive and in which the milk can practically not be degassed due to the short residence time of the milk in the measuring chamber or as they may occur at the end of a milking cycle where the same amount of air is mixed with increasingly smaller milk quantities.

Figure 8:
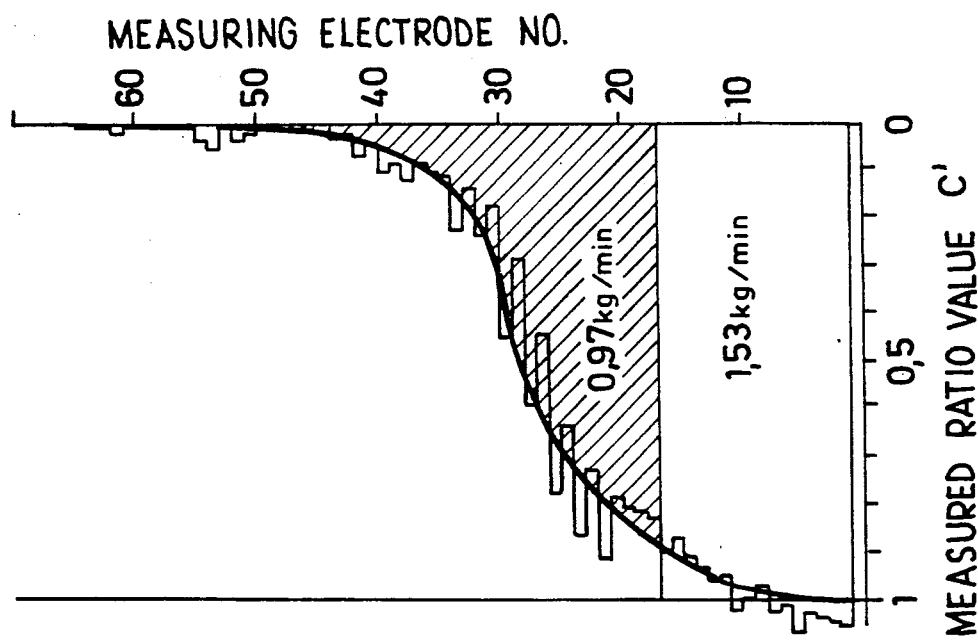
FIG. 8 shows a graphic representation measured according to FIG. 7 during the same measuring cycle at a later point in time.
Figure 7:
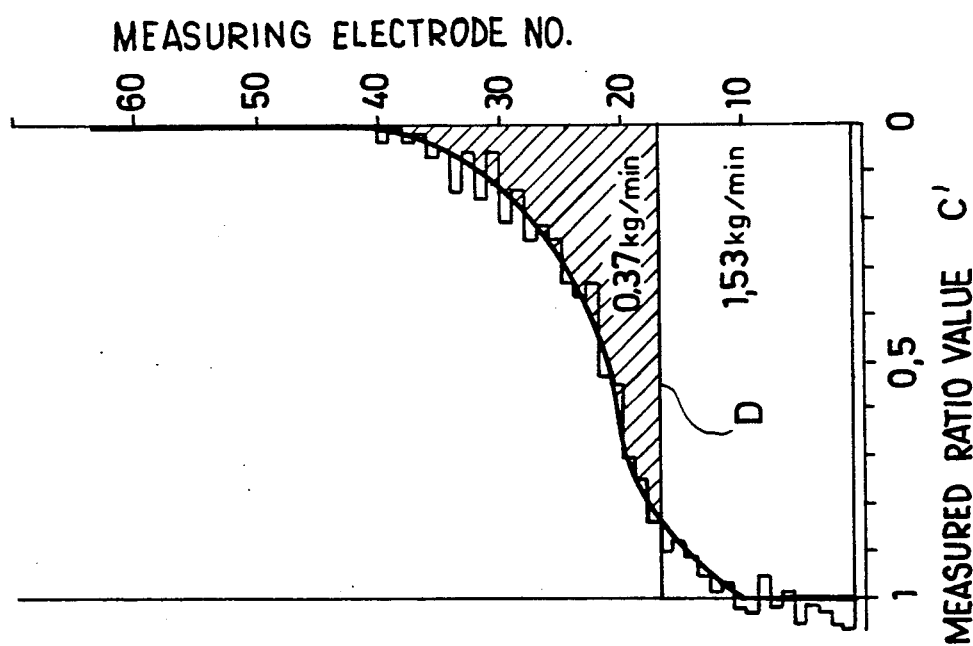
FIG. 7 shows a graphic representation of the measured ratio value c' for the individual measuring electrodes at a point in time within a measuring cycle.

Graphic representations are shown in FIGS. 7 and 8, which represent practically snapshots of the foam profile during a milk flow measurement at different times during one and the same milking cycle of a cow. The measured ratio value c' is in each case plotted on the abscissa in the graphic representations, while the measuring electrodes which are vertically staggered with respect to each other are drawn on the ordinate at individual distances. 64 electrodes are indicated in the representation. As already stated above the total scanning of the electrodes by the multiplexer takes place during a time in the order of about 0.1 seconds. As can be seen from FIG. 7 the electrode have a measuring value of the ratio value c' of 1 up to the height of the measuring electrode 10. That is to say up to this height pure or degassed milk is present. The measuring electrodes located above it, i.e. the electrodes Nos. 10 to 40 have on the other hand already a ratio value deviating from 1.

In the measurement represented in FIG. 8 only the lowermost electrodes show a measuring value of the ratio value c' of about 1. The electrodes 5 to 60 located above show in each case a value smaller than 1.

The curves represented in FIGS. 7 and 8 show very clearly that the milk mass contained in the foam can by no means be simply neglected during the measurements as this has mostly been the case so far in the prior art. If one would make a section in accordance with the shown line D or D' at the points where they reach in each case the value c'=0.9 in both curves, i.e. at points at which it could be assumed that the liquid share contained in the foam corresponds approximately to the amount of liquid which is already replaced by air in the part of the milk quantity located below the sectional line D or D', the considerable differences in the milk share in the foam become evident.

The milk share located below the sectional line D or D' contributes with 1.53 kg/min to the milk flow through the gap. An extremely different quantity of milk mass is contained in the foam share located below the sectional lines D or D'. Therefore the milk mass in FIG. 7 only contributes with 0.37 kg/min. to the milk flow, while the milk quantity contained in the comparable foam profile of FIG. 8 contributes with 0.97 kg/min. to the milk flow.

Figure 9:
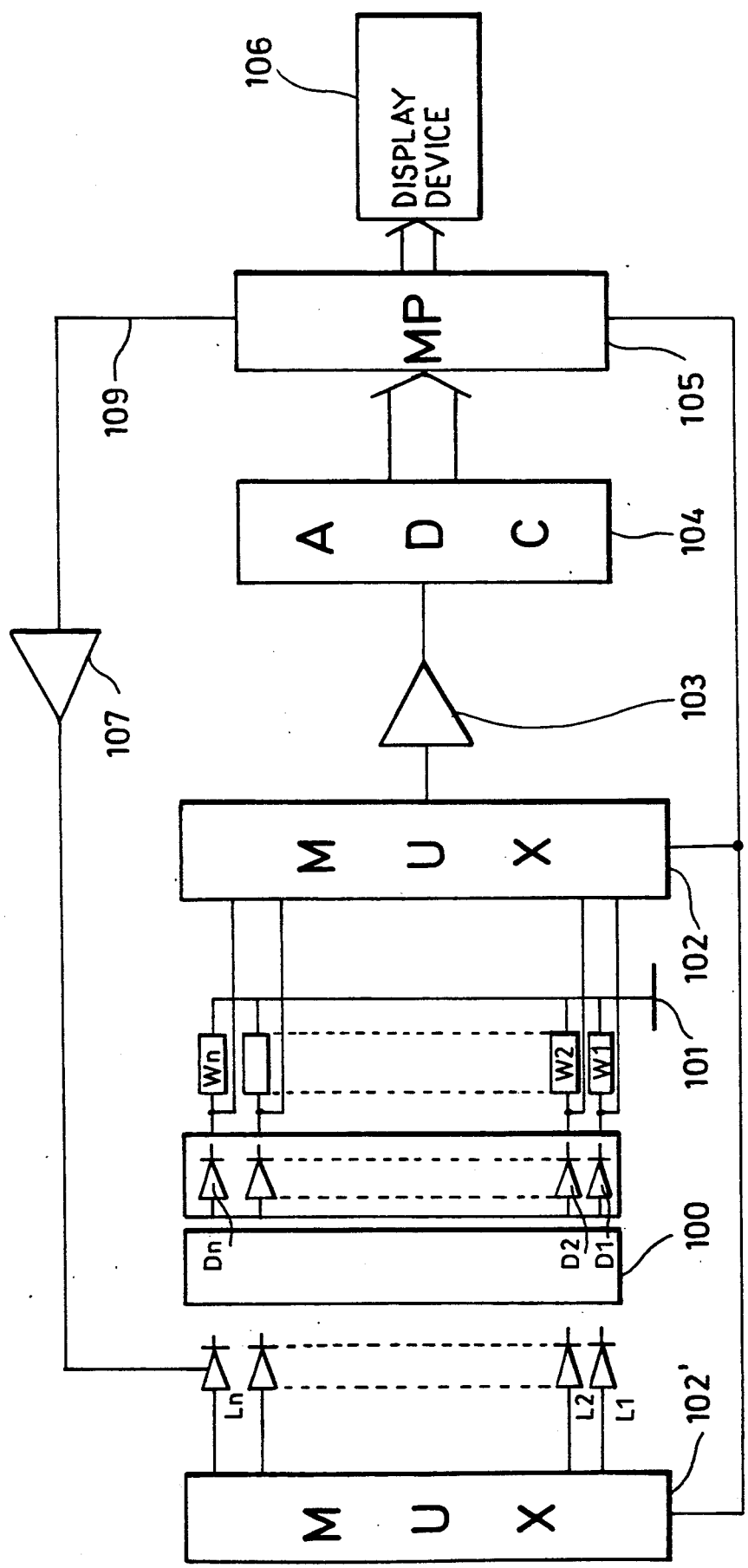
FIG. 9 shows a schematic representation of another embodiment of the invention, in which the measurement of the ratio figure is effected optically and a corresponding circuit arrangement.

Another embodiment according to the invention is described by means of FIG. 9, in which not the resistance of the milk is measured on the measuring path as measuring value, but the light transmitting capacity at predetermined height levels.

The obtained milk is guided into a milking chamber being pervious to infrared rays and is either collected in the same or accumulated in accordance with the measuring arrangement of FIG. 8. Several light sources (light-emitting diodes) L1 to Ln are disposed at several height levels along one side of this measuring chamber. At corresponding height photodiodes $D_1$ to $D_n$ are disposed on the side of the measuring chamber 100 not facing these light-emitting diodes. The light-emitting diodes are either all driven jointly via a driver circuit 107 or successively by means of a multiplexer 102'. The photodiodes $D_1$ to $D_n$ are in each case switched against mass 101 via electrical resistors $W_1$ to $W_n$. The voltage drop occurring at the resistors against mass can be picked off via a multiplexer 102. The multiplexer 102 is suitably synchronized with the multiplexer 102'. The output of the multiplexer 102 is transmitted to an analog-to-digital converter 104 via an amplifier 103, whose digital output signal is supplied to a microprocessor 105. The measuring result obtained by means of the microprocessor can then be displayed on a display means 106. Successive measurements can be controlled by the microprocessor 105 as it transmits corresponding signals to the multiplexer via the line 108 or to the driver circuit 107 via the line 109.

The working method of the measuring device is as follows:

At a specific point in time the microprocessor 105 emits a control signal to the driver 107, which applies a voltage to all light-emitting diodes $L_1$ to $L_n$ via a corresponding circuit. At the same time a corresponding start signal is transmitted to the multiplexer 102' via the line 108. The light-emitting diodes L to $L_n$ are successively switched into their light-emitting conditions by the same at predetermined time intervals. The light emitted by the light-emitting diodes—light-emitting diodes producing an infrared light are preferably used—is absorbed by the milk in the measuring vessel 100 in accordance with the air/milk mixture located between a light diode $L_m$ and the associated photodiode $D_m$ on the measuring path. If only air is present an amount of light impinges accordingly on the associated photodiode which is greater than if pure milk is present. According to the respective luminous intensity of a photodiode a current is generated by it which generates a corresponding voltage drop against mass 101 at the associated resistor $W_m$. Since the multiplexer 102 works synchronously to the multiplexer 102', the voltage drop at a resistor $W_m$ is measured at the same time as the associated light-emitting diode $L_m$ is excited. The respectively measured voltage drops are transmitted to the analog-to-digital converter via the multiplexer 12 and the amplifier 103 and further transmitted by it to the microprocessor 105 as a digitized signal. The same stores the measured voltage drops or voltage values $U_1$ to $U_n$. As already in the measuring arangement according to FIG. 1 the measuring value which is measured at the height level being closest to the bottom of the measuring vessel 100, that is the measuring path between the light-emitting diode $L_1$ and the photodiode $D_1$ is taken as a reference value $U_1 = V_0$ and stored. Then the ratio $$c = \frac{U_O}{U_m}$$

is preferably formed in each case for each measuring path at each height level 1 to n in the microprocessor. These fractional values represent the ratio value c already described above. The remaining further processing of this ratio value and the measurement of the total milk quantity or of the milk flow is effected in the same fashion as in the example of embodiment according to FIG. 1.

Figure 10:
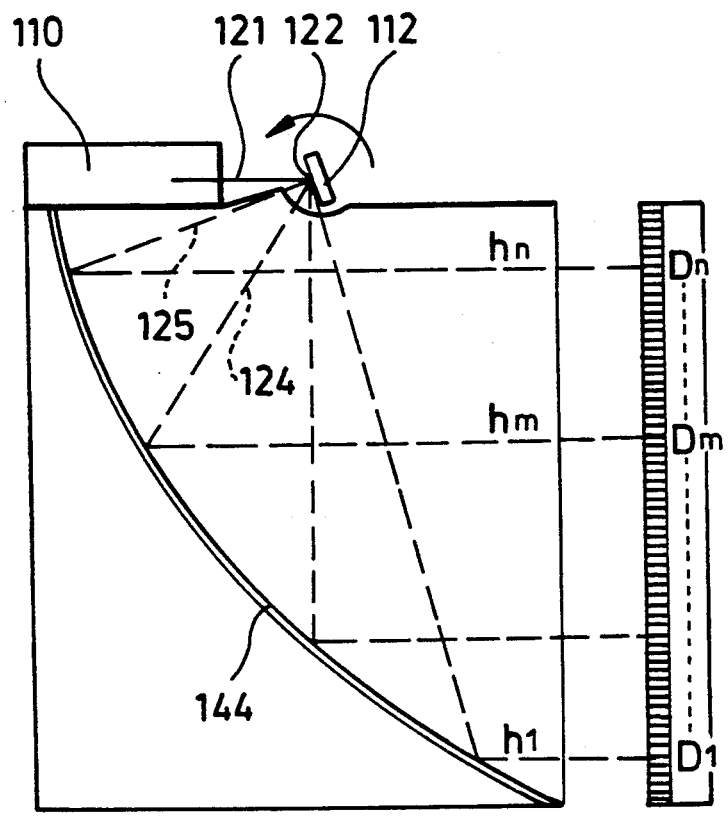
FIG. 10 shows schematically a longitudinal section through a similar measuring device as it is used in FIG. 9, using however only a light source.
Figure 11:
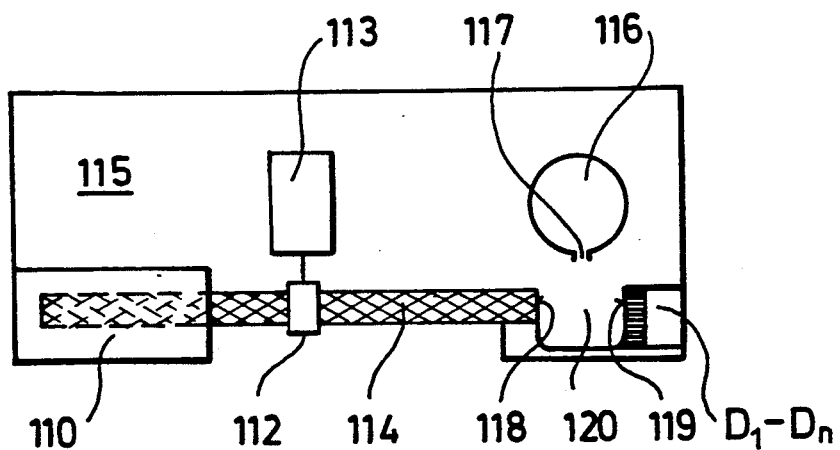
FIG. 11 shows schematically a top view of the arrangement shown in FIG. 10.

An embodiment is represented in FIGS. 10 and 11 with which the arrangement of the light-emitting diodes (light sources) $L_{12}$ to $L_n$ can be replaced by a light source, the remaining circuit arangement being the same. The embodiment shown in FIGS. 10 and 11 serves only for successively generating light signals at the individual height levels which are then received by the photodiodes $D_1$ to $D_n$ after passage through the measuring chamber 100.

The measuring vessel 115 can in particular be gathered from FIG. 11, into which a pipe 116 projects uprightly, in which a vertical longitudinal slot 117 is formed. The milk flown via the other inlet pipes (not shown) flows off via this pipe 116. The measuring vessel 115 has an outwardly projecting lug of a radiolucent material similar to a level height indicator. The opposite side walls 118 and 119 define in each case the measuring path through the milk. The photodiodes $D_1$ to $D_n$ are disposed above each other along the side wall 119 in terms of height as it can be best gathered from FIG. 10. A laser 110 is disposed above the measuring chamber, whose beam impinges on a rotatable mirror 112. The mirror 112 can be adjusted in its angular position via an adjusting motor 113. A reflecting surface 114 which is part of a parabolic mirror is disposed below the rotatable mirror 112 and the laser 110. This reflecting surface 114 is disposed in such fashion with respect to the impingement point 122 of the laser beam 121 on the rotatable mirror 112 that this impingement point is in the focus of the parabolic mirror 114. Accordingly the laser beam 121 is in each case deflected in accordance with the rotational position of the mirror 112 in different directions according to the beams 123, 124 or 125, which are deflected in each case after reflection at the parabolic mirror 114 in beams being in parallel to each other which extend in parallel to each other in accordance with the provided arrangement and are at corresponding height levels $h_1$, $h_m$ and $h_n$. That is to say a corresponding light beam can be produced successively at the individual height levels by a controlled rotation of the mirror 112. The light attenuated on the respective measuring path by absorption or scattering is then received by the photodiodes $D_1$ to $D_n$ associated to the respective height level. The further processing of these signals is effected by a measuring and circuit arrangement as in FIG. 9. (The light could also be introduced by a light conductor arrangement of fibre glass at the height levels instead of by the mirror arrangement.)

Figure 12:
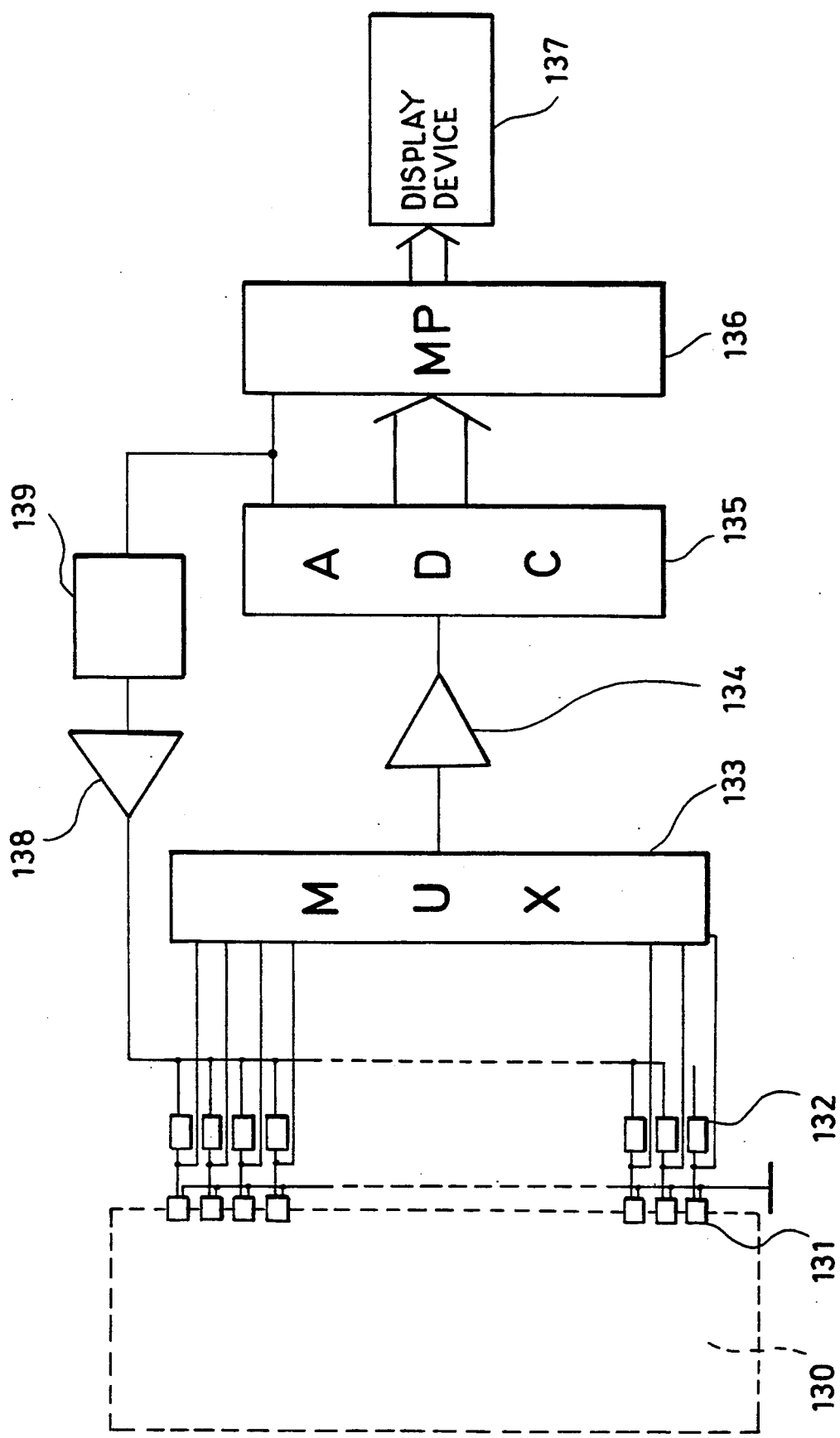
FIG. 12 shows schematically a further embodiment of the invention with an associated circuit, in which the ratio value is measured using the different thermal conductivity of a milk/air mixture.

An embodiment is reprsented in FIG. 12, in which a value coresponding to the milk/air ratio can be measured by means of the thermal conductivity changing due to the air portion in the milk.

PTC temperature sensors disposed vertically in staggered relationship project into a measuring vessel 130. Constant current sources 132 are connected to them, whose heating performance can be controlled via adjustment elements 138, 139. The temperature obtained at each PTC temperature sensor can be scanned via a multiplexer 133 and the signals obtained from it can be supplied to an analog-to-digital converter of a microprocessor via an amplifier 134. The measuring result of the microprocessor can be displayed on a display 137. The adjustment elements 138, 139 for controlling the heating performance can be controlled via the microprocessor.

The device works in such fashion that a constant heating performance controlled by the adjustment elements 138, 139 is supplied to the superimposed temperature sensors 2 to n, while no heating current is supplied to the first PTC temperature sensor being at the first height level or near the bottom of the measuring vessel. After a temporary switching off of the constant heating performance of a temperature sensor its temperature is measured by measuring the resistance value of an associated resistor. The corresponding temperature of the temperature sensor can be calculated from this. This temperature is compared with the temperature of the temperature sensor 1. The resistances measured in accordance with the respective temperature are in each case related to the resistance of the unheated temperature sensor. The respective ratio value C can be ascertained from this in the manner already described for each temperature sensor at each height level.

SUMMARY

It is difficult to determine the quantity or the flow quantity of the foaming liquid by means of a volume measurement in foaming liquids. Now a process and a device are indicated with which the specific density of the liquid/air mixture can at first be determined at different height levels and processes and devices are described with which the total amount of liquid or the flow quantity of the liquid, in particular of milk can be measured by means of these measurements.

The embodiments of the invention in which an exclusive property or privilege is claimed are defined as follows:

1. A process for the measurement of the mass of a foaming liquid, in particular for the measurement of milk mixed with air, in which a measuring value ($I_m$) depending on one parameter of the liquid is respectively measured with the liquid contained in a vessel at several different height levels, comprising the steps wherein a reference value ($I_O$) is measured on a reference measuring path containing substantially degassed liquid, wherein as a function of the fact whether a corresponding measuring value ($I_L$) measured in air is greater or smaller than the reference measuring value ($I_O$) obtained on the reference measuring path, a ratio value ($c'_m$) corresponding to the ratio from the division of one of the reference measuring value ($I_O$) and the measuring value ($I_m$) at this height level by the other is formed for each height level, so that the ratio value ($c'_m$) is equal to 1 for the degassed liquid and substantially equal to zero for air and wherein the volume ($V_m$) between one height level and the next lower height level or the bottom of the vessel is determined in each case and wherein for each height level the ratio value ($c'_m$) is multiplied by the value of the volume ($V_m$) and by the value for the specific density ($\rho$) of the degassed liquid to form the product ($c'_m \times \rho \times V_m$) and wherein for determining the entire liquid mass (G) the sum of all products formed in this fashion is formed across all height levels (n) in accordance with $$G = \sum_{m=1}^{n} c'_m \times V_m \times \rho$$

2. A milk quantity measuring process according to claim 1, in which the milk mass is determined batchwise, by letting milk flow continuously into a measuring vessel and the supply of the milk is interrupted if a predetermined measuring value is reached and the milk is then allowed to flow out completely or until the reaching of a second predetermined measuring value, before the process is repeated, wherein during the flowing in of milk into the measuring vessel, the milk mass is continuously determined and the flowing in of milk is interrupted upon the reaching of a predetermined first milk mass, wherein during the flowing out of the milk the milk mass in the milk vessel is continuously determined, wherein the flowing out of the milk is interrupted upon the reaching of a predetermined second milk mass, wherein the difference is formed from the first and second milk mass to determine the milk mass per batch, wherein the process is repeated until the end of the milk flow in a milking cycle, wherein the milk mass is computed in accordance with the number of the batches and wherein the milk mass collected in the measuring vessel at the end of the milking cycle is determined and added to the already computed milk mass.

3. The process according to claim 2, wherein the milk is allowed to flow out after the reaching of a predetermined first milk mass in the measuring vessel, wherein at the end of the aforementioned outflow of milk the residual milk mass possibly remaining in the foam is determined and wherein for determination of the milk mass per batch the difference between the first predetermined milk mass and the residual milk mass in the foam is formed.

4. The process according to claim 1, wherein the milk obtained in one milking cycle is guided into a milk vessel, wherein the supply of the milk is interrupted at predetermined time intervals and wherein the milk mass present in the measuring vessel at this point in time is determined, wherein this milk mass is carried off from the milk vessel as a batch before the inlet to the milk vessel is opened again and wherein the milk mass measured in the individual batches is added up till the end of the milk flow.

5. The process according to claim 1, wherein the milk obtained in one milking cycle is guided into a measuring vessel, wherein upon the reaching of a predetermined milk mass or at predetermined time intervals the milk is decanted as a batch from the measuring vessel and wherein the milk quantities measured in the individual batches are added up till the end of the milk flow.

6. The process according to claim 1, wherein liquid is supplied to the vessel, wherein liquid flows continuously via a calibrated opening and wherein the flow flowing off via the calibrated opening is computed due to the mass of liquid measured above the height level of the calibrated opening and the resultant hydrostatic pressure.

7. The process according to claim 1, wherein a cylindrical vessel is used as a vessel.

8. The process according to claim 1, wherein the height levels have equal height distances from each other.

9. The process according to claim 1, wherein the reference measuring value is measured on a reference measuring path which is proximate from the bottom of the vessel.

10. The process according to claim 1, wherein the measuring path is on the first height level above the bottom of the vessel and services at the same time as a reference measuring path.

11. The process according to claim 1, wherein measurements of electric resistance is carried out at each height level.

12. The process according to claim 1, wherein measurements of electric conductance is carried out at each height level.

13. The process according to claim 1, wherein measurements of light transmission is carried out at each height level.

14. The process according to claim 1, wherein measurements of absorption of IR rays is carried out at each height level.

15. The process according to claim 1, wherein measurements of thermal conduction are carried out at each height level.

16. The process according to claim 1, wherein for the calibration of the total mass (G) of liquid obtained, all measured ratio values ($c_m$) are raised to a higher power with one and the same exponent grater than 0 for forming corrected ratio values ($c'_m$).

17. The process according to claim 1, wherein for avoiding errors caused by different conditions on the individual measuring paths, measurements are carried out with a calibrating liquid being the same for all measuring paths, wherein a mean value is formed from the obtained measuring values, and wherein the measuring value of each measuring path is weighted with a correction factor computed in accordance of the deviation of its measuring value from the mean value.

18. The process according to claim 1, wherein the scanning of the measuring values at all height levels is carried out in each case during a time which is in the range of 0.1 seconds to 1.0 second.

19. A device for measuring the mass of a foaming liquid, in particular for the measurement of the mass of milk mixed with air, comprising a vessel and at least one measuring device with which a measuring value ($I_m$) depending on one parameter can be measured at several different height levels of the vessel, wherein a reference measuring path containing substantially degassed liquid is provided, wherein a device is provided which forms for each height level a ratio value ($c'_m$) in accordance with the division of one of the reference measuring value ($I_O$) and the measuring value ($I_m$) at this height level by the other as a function of the fact whether a corresponding measuring value ($I_L$) measured in air is greater or smaller than the reference measuring value ($I_O$) obtained on the reference measuring path, so that the ratio value ($c'_m$) is equal to 1 for the degassed liquid and substantially equal to zero for air and wherein a multiplying element is provided with which each ratio value ($c'_m$) is multiplied by the value for the specific density $\rho$ of the degassed liquid and by the size of the value ($V_m$) enclosed between the accorded height level and the height level located below it in the vessel so that the product $c'_m \times V_m \times \rho$ is formed and that an adding means is provided for adding the products formed for all height levels (n) to indicate the total mass of liquid (G) as $$G = \sum_{m=1}^{n} c'_m \times V_m \times \rho$$

20. The device according to claim 19, wherein the liquid quantity measuring device is provided at a measuring chamber of a batchwise measuring device.

21. The device according to claim 19, wherein the reference measuring path is proximate from the bottom of the vessel.

22. The device according to claim 19, wherein the measuring value on the height level directly above the bottom of the vessel serves as a reference measuring value.

23. The device according to claim 19, wherein the vessel is a cylindrical vessel.

24. The device according to claim 19, wherein the height levels have equal height distances from each other.

25. The device according to claim 19, wherein an electrode is disposed at the level of each height level, and wherein a joint counter-electrode is provided.

26. The device according to claim 25, wherein said electrode and said counter-electrode are provided on a common electrode member.

27. The device according to claim 19 wherein an electrode is disposed at the level of each height level and, wherein a counter-electrode is provided opposite to each electrode.

28. The device according to claim 25, wherein electrical conductance is measured as a measuring value.

29. The device according to claim 25, wherein electrical resistance of the measuring path is measured as a measuring value.

30. The device according to claim 28, wherein the measurement is carried out with an a-c voltage.

31. The device according to claim 30, wherein the measurements are carried out with a frequency between 200 Hz and 80 kHz.

32. The device according to claim 31, wherein the measurements are carried out with a frequency of 2 kHz.

33. The device according to claim 25, wherein the measurement is carried out with an a-c voltage.

34. The device according to claim 33, wherein the measurements are carried out with a frequency between 200 Hz and 80 kHz.

35. The device according to claim 34, wherein the measurements are carried out with a frequency of 2 kHz.

36. The device according to claim 33, wherein the a-c voltage is sine-shaped.

37. The device according to claim 33, wherein the a-c voltage is triangularly shaped.

38. The device according to claim 36, wherein the measurements are carried out with a frequency between 200 Hz and 80 kHz.

39. The device according to claim 38, wherein the measurements are carried out with a frequency of 2 kHz.

40. The device according to claim 25, wherein for preventing a d-c portion, a decoupling capacitor is switched between a voltage source and said at least one of the joint counter-electrode and the counter-electrodes.

41. The device according to claim 40, wherein the measurements are carried out with a frequency between 200 Hz and 80 kHz.

42. The device according to claim 41, wherein the measurements are carried out with a frequency of 2 kHz.

43. The device according to claim 25, wherein the electrodes are substantially circular and have a diameter in the range of 0.5 to 1.2 mm.

44. The device according to claim 25, wherein the electrodes are substantially circular and have a diameter of 0.8 mm.

45. The device according to claim 25, wherein the electrodes are disposed at a height distance in the range of 1 to 8 mm.

46. The device according to claim 25, wherein the electrodes are disposed at a height distance of 1.5 mm.

47. The device according to claim 27, wherein the distance been each electrode and its respective counter-electrode is in the range of 2 and 150 mm.

48. The device according to claim 27, wherein the distance between each electrode and its respective counter-electrode is 4 mm.

49. The device according to claim 19, wherein a light source is provided at each height level, by means of which a light ray is radiated through the liquid contained in the vessel, and wherein an electrooptical transducer is provided for each height level, which electrooptical transducer generates an electrical measuring value signal corresponding to the received luminous intensity.

50. The device according to claim 19, wherein an IR light source and an optical light guiding device are provided, by means of which the IR light ray can be radiated successively at different height levels through the liquid contained in the vessel, and wherein an electrooptical transducer is provided for each height level, which electrooptical transducer generates a measuring value signal corresponding to the received luminous intensity.

51. The device according to claim 19, further including PTC temperature sensors disposed at the vessel at different height levels, constant current sources which supply in each case a constant heating capacity to the PTC temperature sensors and resistance measuring circuits which determine the value of resistance corresponding to the temperature of the corresponding PTC temperature sensor.

52. The device according to claim 19, wherein said liquid is milk mixed with air.

* * * * *